(12) United States Patent
Kahook et al.

(10) Patent No.: US 11,406,491 B2
(45) Date of Patent: Aug. 9, 2022

(54) MODULAR INTRAOCULAR LENS DESIGNS, TOOLS AND METHODS

(71) Applicants: ClarVista Medical, Inc., Aliso Viejo, CA (US); The Regents of the University of Colorado, a body corporate, Denver, CO (US)

(72) Inventors: Malik Y. Kahook, Denver, CO (US); Glenn Sussman, Laguna Niguel, CA (US); Paul McLean, North Oaks, MN (US); Andrew Schieber, Aliso Viejo, CA (US)

(73) Assignees: Alcon Inc, Fribourg (CH); The Regents of the University of Colorado, Denver, CO (US)

( * ) Notice: Subject to any disclaimer, the term of this patent is extended or adjusted under 35 U.S.C. 154(b) by 816 days.

(21) Appl. No.: 15/890,914

(22) Filed: Feb. 7, 2018

(65) Prior Publication Data

US 2018/0161153 A1    Jun. 14, 2018

Related U.S. Application Data

(63) Continuation of application No. 15/218,658, filed on Jul. 25, 2016, now Pat. No. 9,925,040, which is a
(Continued)

(51) Int. Cl.
*A61F 2/16* (2006.01)

(52) U.S. Cl.
CPC .............. *A61F 2/1648* (2013.01); *A61F 2/16* (2013.01); *A61F 2/1613* (2013.01); *A61F 2/167* (2013.01);
(Continued)

(58) Field of Classification Search
CPC ...... A61F 2/16; A61F 2/1601; A61F 2/16015; A61F 2/1613; A61F 2/1648;
(Continued)

(56) References Cited

U.S. PATENT DOCUMENTS

| 3,937,222 A | 2/1976 | Banko |
| 4,092,743 A | 6/1978 | Kelman |

(Continued)

FOREIGN PATENT DOCUMENTS

| CA | 3 002 085 A1 | 5/2017 |
| CN | 101039635 A | 9/2007 |

(Continued)

OTHER PUBLICATIONS

PCT International Search Report and Written Opinion for International Application No. PCT/US2017/031066, dated Nov. 6, 2018 (9 pages).

(Continued)

*Primary Examiner* — William H Matthews
(74) *Attorney, Agent, or Firm* — Bookoff McAndrews, PLLC

(57) ABSTRACT

Modular IOL systems including a base and a lens, wherein the lens includes fixed and actuatable tabs for connection to the base. The modular IOL allows for the lens to be adjusted or exchanged while leaving the base in place, either intraoperatively or post-operatively. Drug delivery capabilities and/or sensing capabilities may be incorporated into the base. Injector devices may be used to facilitate placement of the base and the lens sequentially or simultaneously into the eye.

18 Claims, 21 Drawing Sheets

Related U.S. Application Data continuation of application No. 15/150,360, filed on May 9, 2016, now Pat. No. 9,421,088, which is a continuation of application No. 14/828,083, filed on Aug. 17, 2015, now Pat. No. 9,364,316.

(60) Provisional application No. 62/110,241, filed on Jan. 30, 2015.

(52) U.S. Cl.
CPC ........... *A61F 2/1664* (2013.01); *A61F 2/1672* (2013.01); *A61F 2/1678* (2013.01); *A61F 2002/169* (2015.04); *A61F 2002/1681* (2013.01); *A61F 2002/1689* (2013.01); *A61F 2002/16902* (2015.04); *A61F 2002/16905* (2015.04); *A61F 2220/0033* (2013.01); *A61F 2250/006* (2013.01); *A61F 2250/0067* (2013.01); *A61F 2310/0097* (2013.01)

(58) Field of Classification Search
CPC ............ A61F 2/1694; A61F 2002/1681; A61F 2002/169; A61F 2002/16901
See application file for complete search history.

(56) References Cited

U.S. PATENT DOCUMENTS

| | | | |
|---|---|---|---|
| 4,168,547 A | 9/1979 | Konstantinov et al. | |
| 4,409,691 A | 10/1983 | Levy | |
| 4,435,856 A | 3/1984 | L'Esperance | |
| 4,681,102 A | 7/1987 | Bartell | |
| 4,693,245 A | 9/1987 | Pao | |
| 4,741,330 A | 5/1988 | Hayhurst | |
| 4,769,035 A | 11/1988 | Kelman | |
| 4,816,031 A | 3/1989 | Pfoff | |
| 4,828,558 A | 5/1989 | Kelman | |
| 4,842,601 A | 6/1989 | Smith | |
| 4,878,910 A | 11/1989 | Koziol et al. | |
| 4,911,715 A | 3/1990 | Kelman | |
| 4,932,971 A | 6/1990 | Kelman | |
| 4,950,272 A | 8/1990 | Smirmaul | |
| 4,960,418 A | 10/1990 | Tennant | |
| 5,026,396 A | 6/1991 | Darin | |
| 5,030,230 A | 7/1991 | White | |
| 5,098,444 A | 3/1992 | Feaster | |
| 5,123,905 A | 6/1992 | Kelman | |
| 5,133,747 A | 7/1992 | Feaster | |
| 5,147,369 A | 9/1992 | Wagner | |
| 5,152,788 A | 10/1992 | Isaacson et al. | |
| 5,201,762 A | 4/1993 | Hauber | |
| 5,222,981 A | 6/1993 | Werblin | |
| 5,304,182 A | 4/1994 | Rheinsish et al. | |
| 5,354,335 A | 10/1994 | Lipshitz et al. | |
| 5,358,520 A | 10/1994 | Patel | |
| 5,366,502 A | 11/1994 | Patel | |
| 5,378,475 A | 1/1995 | Smith et al. | |
| 5,391,202 A | 2/1995 | Lipshitz et al. | |
| 5,395,378 A | 3/1995 | McDonald | |
| 5,410,375 A | 4/1995 | Fiala | |
| 5,417,369 A | 5/1995 | Lipson | |
| 5,507,805 A | 4/1996 | Koeniger | |
| 5,578,081 A | 11/1996 | McDonald | |
| 5,616,120 A | 4/1997 | Andrew et al. | |
| 5,628,795 A | 5/1997 | Langerman | |
| 5,628,798 A | 5/1997 | Eggleston et al. | |
| 5,728,155 A | 3/1998 | Anello et al. | |
| 5,769,890 A | 6/1998 | McDonald | |
| 5,814,103 A | 9/1998 | Lipshitz et al. | |
| 5,824,074 A | 10/1998 | Koch | |
| 5,860,985 A | 1/1999 | Anschutz | |
| 5,876,442 A | 3/1999 | Lipshitz et al. | |
| 5,895,422 A | 4/1999 | Hauber | |
| 5,902,598 A | 5/1999 | Chen et al. | |
| 5,928,283 A | 7/1999 | Gross et al. | |
| 5,944,725 A | 8/1999 | Cicenas et al. | |
| 5,964,802 A | 10/1999 | Anello et al. | |
| 5,968,094 A | 10/1999 | Werblin et al. | |
| 5,984,962 A * | 11/1999 | Anello | A61F 2/1613 623/6.46 |
| 6,027,531 A | 2/2000 | Tassignon | |
| 6,066,171 A | 5/2000 | Lipshitz et al. | |
| 6,113,633 A | 9/2000 | Portney | |
| 6,136,026 A * | 10/2000 | Israel | A61F 2/16 623/6.11 |
| 6,197,057 B1 | 3/2001 | Peyman et al. | |
| 6,197,058 B1 | 3/2001 | Portney | |
| 6,228,113 B1 | 5/2001 | Kaufman | |
| 6,231,603 B1 | 5/2001 | Lang et al. | |
| 6,277,146 B1 | 8/2001 | Peyman et al. | |
| 6,280,471 B1 | 8/2001 | Peyman et al. | |
| 6,358,280 B1 | 3/2002 | Herrick | |
| 6,413,276 B1 | 7/2002 | Werblin | |
| 6,423,094 B1 | 7/2002 | Sarfarazi | |
| 6,454,801 B1 | 9/2002 | Portney | |
| 6,464,725 B2 | 10/2002 | Skotton | |
| 6,488,708 B2 | 12/2002 | Sarfarazi | |
| 6,537,281 B1 | 3/2003 | Portney | |
| 6,551,354 B1 | 4/2003 | Ghazizadeh et al. | |
| 6,554,859 B1 | 4/2003 | Lang et al. | |
| 6,558,420 B2 | 5/2003 | Green | |
| 6,596,026 B1 | 7/2003 | Gross et al. | |
| 6,599,317 B1 | 7/2003 | Weinschenk, III et al. | |
| 6,616,692 B1 | 9/2003 | Glick et al. | |
| 6,638,304 B2 | 10/2003 | Azar | |
| 6,685,741 B2 | 2/2004 | Landreville et al. | |
| 6,695,881 B2 | 2/2004 | Peng et al. | |
| 6,764,511 B2 | 7/2004 | Zadno-Azizi et al. | |
| 6,767,363 B1 | 7/2004 | Bandhauer et al. | |
| 6,786,934 B2 | 9/2004 | Zadno-Azizi et al. | |
| 6,797,004 B1 | 9/2004 | Brady et al. | |
| 6,818,017 B1 | 11/2004 | Shu | |
| 6,846,326 B2 | 1/2005 | Zadno-Azizi et al. | |
| 6,858,040 B2 | 2/2005 | Nguyen et al. | |
| 6,899,732 B2 | 5/2005 | Zadno-Azizi et al. | |
| 6,926,736 B2 | 8/2005 | Peng et al. | |
| 6,960,231 B2 | 11/2005 | Tran | |
| 6,969,403 B2 | 11/2005 | Peng et al. | |
| 6,972,032 B2 | 12/2005 | Aharoni et al. | |
| 6,972,034 B2 | 12/2005 | Tran et al. | |
| 6,991,651 B2 | 1/2006 | Portney | |
| 7,008,447 B2 | 3/2006 | Koziol | |
| 7,041,134 B2 | 5/2006 | Nguyen et al. | |
| 7,081,134 B2 | 7/2006 | Cukrowski | |
| 7,087,080 B2 | 8/2006 | Zadno-Azizi et al. | |
| 7,097,660 B2 | 8/2006 | Portney | |
| 7,101,397 B2 | 9/2006 | Aharoni | |
| 7,118,596 B2 | 10/2006 | Zadno-Azizi et al. | |
| 7,122,053 B2 | 10/2006 | Esch | |
| 7,125,422 B2 | 10/2006 | Woods et al. | |
| 7,186,266 B2 | 3/2007 | Peyman | |
| 7,198,640 B2 | 4/2007 | Nguyen | |
| 7,220,278 B2 | 5/2007 | Peyman | |
| 7,223,288 B2 | 5/2007 | Zhang et al. | |
| 7,226,478 B2 | 6/2007 | Ting et al. | |
| 7,238,201 B2 | 7/2007 | Portney et al. | |
| 7,300,464 B2 | 11/2007 | Tran | |
| 7,316,713 B2 | 1/2008 | Zhang | |
| 7,452,378 B2 | 11/2008 | Zadno-Azizi et al. | |
| 7,582,113 B2 | 9/2009 | Terwee | |
| 7,591,849 B2 | 9/2009 | Richardson | |
| 7,645,299 B2 | 1/2010 | Koziol | |
| 7,662,179 B2 | 2/2010 | Sarfarazi | |
| 7,727,277 B2 | 6/2010 | Aharoni et al. | |
| 7,736,390 B2 | 6/2010 | Aharoni et al. | |
| 7,780,729 B2 | 8/2010 | Nguyen et al. | |
| 7,811,320 B2 | 10/2010 | Werblin | |
| 7,857,850 B2 | 12/2010 | Mentak et al. | |
| 7,871,437 B2 | 1/2011 | Hermans et al. | |
| 7,918,886 B2 | 4/2011 | Aharoni et al. | |
| 7,985,253 B2 | 7/2011 | Cumming | |
| 7,993,399 B2 | 8/2011 | Peyman | |
| 7,998,198 B2 | 8/2011 | Angelopoulos et al. | |
| 8,012,204 B2 | 9/2011 | Weinschenk, III et al. | |

(56) References Cited

U.S. PATENT DOCUMENTS

| | | |
|---|---|---|
| 8,034,106 B2 | 10/2011 | Mentak et al. |
| 8,034,107 B2 | 10/2011 | Stenger |
| 8,034,108 B2 | 10/2011 | Bumbalough |
| 8,062,361 B2 | 11/2011 | Nguyen et al. |
| 8,066,768 B2 | 11/2011 | Werblin |
| 8,066,769 B2 | 11/2011 | Werblin |
| 8,128,693 B2 | 3/2012 | Tran et al. |
| 8,137,399 B2 | 3/2012 | Glazier et al. |
| 8,167,941 B2 | 5/2012 | Boyd et al. |
| 8,182,531 B2 | 5/2012 | Hermans et al. |
| 8,187,325 B2 | 5/2012 | Zadno-Azizi et al. |
| 8,197,541 B2 | 6/2012 | Schedler |
| 8,273,123 B2 | 9/2012 | Ben Nun |
| 8,287,593 B2 | 10/2012 | Portney |
| 8,377,124 B2 | 2/2013 | Hong et al. |
| 8,425,597 B2 | 4/2013 | Glick et al. |
| 8,486,142 B2 | 7/2013 | Bumbalough |
| 8,579,972 B2 | 11/2013 | Rombach |
| 8,663,235 B2 | 3/2014 | Tassignon |
| 8,728,158 B2 | 5/2014 | Whitsett |
| 8,758,434 B2 | 6/2014 | Scott |
| 8,900,300 B1 | 12/2014 | Wortz |
| 9,011,532 B2 | 4/2015 | Bumbalough |
| 9,095,424 B2 | 8/2015 | Kahook et al. |
| 9,125,736 B2 | 9/2015 | Kahook |
| 9,186,244 B2 | 11/2015 | Silvestrini et al. |
| 9,198,752 B2 | 12/2015 | Woods |
| 9,204,961 B2 | 12/2015 | Cuevas |
| 9,220,590 B2 | 12/2015 | Beer |
| 9,289,287 B2 | 3/2016 | Kahook |
| 9,364,316 B1 | 6/2016 | Kahook |
| 9,387,069 B2 | 7/2016 | Kahook et al. |
| 9,414,907 B2 | 8/2016 | Wortz et al. |
| 9,421,088 B1 | 8/2016 | Kahook et al. |
| 9,504,558 B2 | 11/2016 | Wortz et al. |
| 9,517,127 B2 | 12/2016 | Wortz et al. |
| 9,522,059 B2 | 12/2016 | Wortz et al. |
| 9,522,060 B2 | 12/2016 | Wortz et al. |
| 9,681,946 B2 | 6/2017 | Kahook et al. |
| 9,877,825 B2 | 1/2018 | Kahook et al. |
| 9,925,040 B2 | 3/2018 | Kahook et al. |
| 10,004,596 B2 | 6/2018 | Brady et al. |
| 10,028,824 B2 | 7/2018 | Kahook et al. |
| 10,080,648 B2 | 9/2018 | Kahook et al. |
| 10,111,745 B2 | 10/2018 | Silvestrini et al. |
| 10,159,564 B2 | 12/2018 | Brady et al. |
| 2002/0138140 A1 | 9/2002 | Hanna |
| 2003/0088253 A1 | 5/2003 | Seil |
| 2003/0144733 A1 | 7/2003 | Brady et al. |
| 2003/0158560 A1 | 8/2003 | Portney |
| 2004/0010310 A1 | 1/2004 | Peymen |
| 2004/0106993 A1 | 6/2004 | Portney |
| 2004/0148022 A1 | 7/2004 | Eggleston |
| 2004/0236422 A1 | 11/2004 | Zhang et al. |
| 2004/0243142 A1 | 12/2004 | Siepser |
| 2005/0015144 A1 | 1/2005 | Tran |
| 2005/0021139 A1 | 1/2005 | Shadduck |
| 2005/0027354 A1 | 2/2005 | Brady et al. |
| 2005/0187621 A1 | 5/2005 | Brady |
| 2005/0125058 A1 | 6/2005 | Cumming et al. |
| 2005/0131535 A1 | 6/2005 | Woods |
| 2005/0273163 A1 | 12/2005 | Tran et al. |
| 2006/0111776 A1 | 5/2006 | Glick et al. |
| 2006/0253196 A1 | 11/2006 | Woods |
| 2006/0286147 A1 | 12/2006 | Salamone et al. |
| 2007/0052923 A1 | 3/2007 | Ayyagari et al. |
| 2007/0123981 A1 | 5/2007 | Tassignon |
| 2007/0156236 A1 | 7/2007 | Stenger |
| 2008/0046077 A1 | 2/2008 | Cumming |
| 2008/0103592 A1 | 5/2008 | Maloney |
| 2008/0215147 A1 | 9/2008 | Werblin |
| 2008/0281416 A1 | 11/2008 | Cumming |
| 2009/0005864 A1 | 1/2009 | Eggleston |
| 2009/0062912 A1 | 3/2009 | Rombach |
| 2010/0016964 A1 | 1/2010 | Werblin |
| 2010/0204787 A1 | 8/2010 | Noy |
| 2010/0204790 A1 | 8/2010 | Whitsett |
| 2010/0298933 A1 | 11/2010 | Knox et al. |
| 2011/0040378 A1 | 2/2011 | Werblin |
| 2011/0054600 A1 | 3/2011 | Bumbalough |
| 2011/0251686 A1 | 10/2011 | Masket |
| 2011/0257742 A1 | 10/2011 | Bumbalough |
| 2011/0307058 A1 | 12/2011 | Beer |
| 2011/0313521 A1 | 12/2011 | Angelopoulos |
| 2012/0078364 A1 | 3/2012 | Stenger |
| 2012/0179249 A1 | 7/2012 | Coleman |
| 2012/0209305 A1 | 8/2012 | Deodhar et al. |
| 2012/0323320 A1 | 12/2012 | Simonov et al. |
| 2013/0053954 A1 | 2/2013 | Rao et al. |
| 2013/0066422 A1 | 3/2013 | Dworschak et al. |
| 2013/0184815 A1 | 7/2013 | Roholt |
| 2013/0190868 A1 | 7/2013 | Kahook et al. |
| 2013/0296694 A1 | 11/2013 | Ehlers et al. |
| 2013/0304204 A1 | 11/2013 | Bumbalough |
| 2013/0304206 A1 | 11/2013 | Pallikaris et al. |
| 2013/0310931 A1 | 11/2013 | Kahook et al. |
| 2014/0052246 A1 | 2/2014 | Kahook et al. |
| 2014/0081178 A1 | 3/2014 | Pletcher et al. |
| 2014/0084489 A1 | 3/2014 | Etzkorn |
| 2014/0085599 A1 | 3/2014 | Etzkorn |
| 2014/0085600 A1 | 3/2014 | Pletcher et al. |
| 2014/0085602 A1 | 3/2014 | Ho et al. |
| 2014/0087452 A1 | 3/2014 | Liu et al. |
| 2014/0088381 A1 | 3/2014 | Etzkorn et al. |
| 2014/0098226 A1 | 4/2014 | Pletcher et al. |
| 2014/0180403 A1 | 6/2014 | Silvestrini et al. |
| 2014/0180411 A1 | 6/2014 | Tornambe et al. |
| 2014/0192311 A1 | 7/2014 | Pletcher et al. |
| 2014/0194710 A1 | 7/2014 | Ho et al. |
| 2014/0194713 A1 | 7/2014 | Liu |
| 2014/0194773 A1 | 7/2014 | Pletcher et al. |
| 2014/0371852 A1 | 12/2014 | Aharoni et al. |
| 2015/0105760 A1 | 4/2015 | Rao et al. |
| 2015/0157452 A1 | 6/2015 | Maliarov |
| 2015/0230981 A1 | 8/2015 | Kahook et al. |
| 2016/0030161 A1 | 2/2016 | Brady et al. |
| 2016/0074154 A1 | 3/2016 | Woods |
| 2016/0128826 A1 | 5/2016 | Silvestrini et al. |
| 2016/0157995 A1 | 6/2016 | Beer |
| 2016/0184089 A1 | 6/2016 | Dudee et al. |
| 2016/0235524 A1 | 8/2016 | Wortz et al. |
| 2016/0235587 A1 | 8/2016 | Kahook et al. |
| 2016/0310264 A1 | 10/2016 | Akura |
| 2016/0317286 A1 | 11/2016 | Brady et al. |
| 2016/0317287 A1 | 11/2016 | Silvestrini et al. |
| 2016/0338825 A1 | 11/2016 | Wortz et al. |
| 2017/0119521 A1 | 5/2017 | Kahook et al. |
| 2017/0319332 A1 | 11/2017 | Kahook et al. |
| 2018/0014928 A1 | 1/2018 | Kahook et al. |
| 2018/0177639 A1 | 6/2018 | Rao et al. |
| 2018/0344453 A1 | 12/2018 | Brady et al. |
| 2018/0368974 A1 | 12/2018 | Kahook et al. |
| 2019/0000612 A1 | 1/2019 | Rao et al. |
| 2019/0021848 A1 | 1/2019 | Kahook et al. |
| 2019/0099263 A1 | 4/2019 | Brady et al. |

FOREIGN PATENT DOCUMENTS

| | | |
|---|---|---|
| CN | 101641060 A | 2/2010 |
| CN | 104936553 A | 9/2015 |
| DE | 35 03 690 C1 | 11/1986 |
| DE | 36 26 869 A1 | 2/1988 |
| DE | 10 2007 053 224 A1 | 5/2009 |
| EP | 0 478 929 A1 | 4/1992 |
| EP | 1 138 282 A1 | 10/2001 |
| EP | 1 457 170 A1 | 9/2004 |
| EP | 1 743 601 A1 | 1/2007 |
| EP | 1 862 147 A1 | 12/2007 |
| EP | 2 042 124 A1 | 4/2009 |
| EP | 2332501 A1 | 6/2011 |
| EP | 1 296 616 B1 | 5/2012 |
| EP | 1 871 299 B1 | 8/2012 |
| EP | 2491902 B1 | 8/2012 |
| FR | 2 734 472 A1 | 11/1996 |

(56) References Cited

FOREIGN PATENT DOCUMENTS

| | | |
|---|---|---|
| JP | 62-022641 | 1/1987 |
| JP | 01-097450 | 4/1989 |
| JP | 04-505715 | 10/1992 |
| JP | 06-165793 | 6/1994 |
| JP | 06-189985 | 7/1994 |
| JP | 63-089154 | 4/1998 |
| JP | 2003-505197 | 2/2003 |
| JP | 2003-524503 | 8/2003 |
| JP | 2007-512907 | 5/2007 |
| JP | 2008-525156 | 7/2008 |
| JP | 2008-532617 | 8/2008 |
| JP | 2010-516394 | 5/2010 |
| JP | 2012-040326 | 3/2012 |
| JP | 2013-512033 | 4/2013 |
| JP | 5705529 B2 | 4/2015 |
| RU | 2026652 C1 | 1/1995 |
| WO | WO 94/28825 A1 | 12/1994 |
| WO | WO 96/29956 A1 | 10/1996 |
| WO | WO 03/039335 A2 | 5/2003 |
| WO | WO 2006/023871 A2 | 3/2006 |
| WO | WO 2006/118452 A1 | 11/2006 |
| WO | WO 2008/094518 A1 | 8/2008 |
| WO | WO 2008/108524 A1 | 9/2008 |
| WO | WO 2010/002215 A2 | 1/2010 |
| WO | WO 2012/023133 A1 | 2/2012 |
| WO | WO 2012/071146 A2 | 5/2012 |
| WO | WO 2013/112589 A1 | 8/2013 |
| WO | WO 2013/158942 A1 | 10/2013 |
| WO | WO 2014/099604 A1 | 6/2014 |
| WO | WO 2014/197170 A1 | 12/2014 |
| WO | WO 2014/204575 A1 | 12/2014 |
| WO | WO 2016/022995 A2 | 2/2016 |
| WO | WO 2016/130209 A1 | 8/2016 |

OTHER PUBLICATIONS

PCT International Search Report and Written Opinion for International Application No. PCT/US2013/022752, dated Apr. 19, 2013 (12 pages).

PCT International Search Report and Written Opinion for International Application No. PCT/US2014/037646, dated Aug. 18, 2014 (14 pages).

PCT International Search Report and Written Opinion for International Application No. PCT/US2015/014046, dated Apr. 9, 2015 (14 pages).

PCT International Search Report and Written Opinion for International Application No. PCT/US2015/067035, dated Apr. 12, 2016 (17 pages).

PCT International Search Report and Written Opinion for International Application No. PCT/US2016/060350, dated Jan. 27, 2017 (14 pages).

* cited by examiner

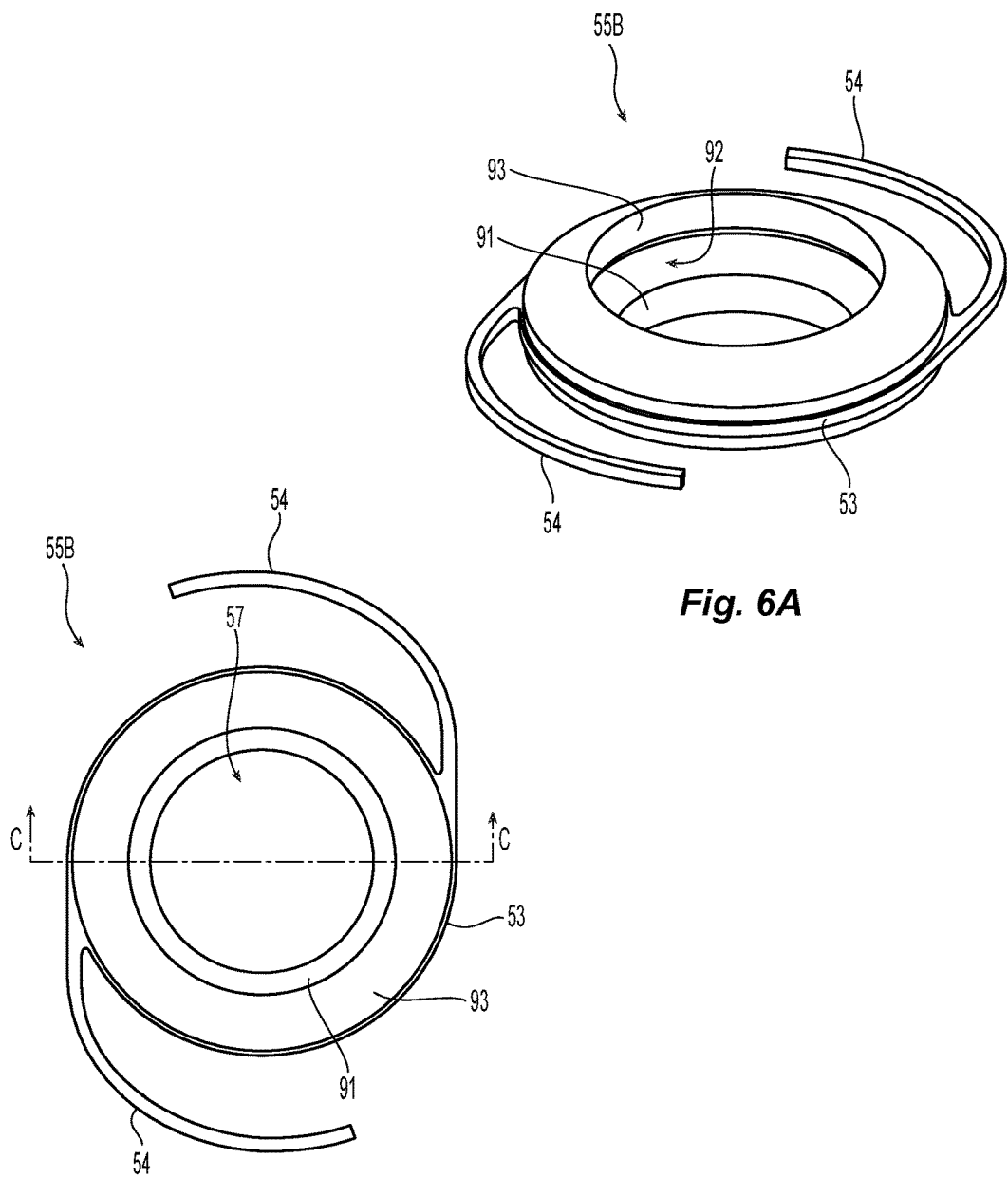
*Fig. 6A*
*Fig. 6B*
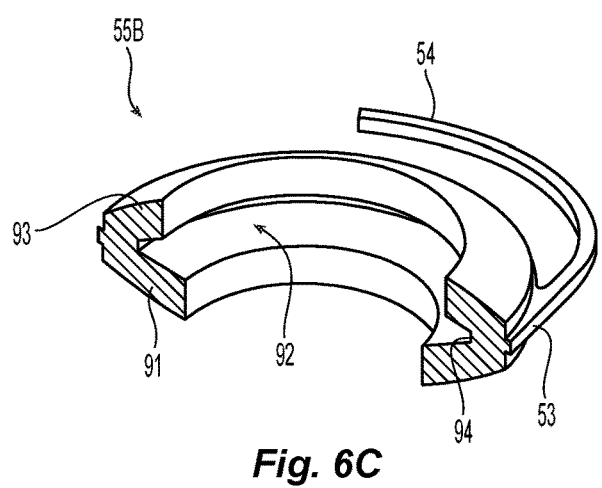
*Fig. 6C*

MODULAR INTRAOCULAR LENS DESIGNS, TOOLS AND METHODS

CROSS-REFERENCE TO RELATED APPLICATIONS

This application is a continuation of U.S. application Ser. No. 15/218,658, filed Jul. 25, 2016, which is a continuation of U.S. application Ser. No. 15/150,360, filed May 9, 2016, now U.S. Pat. No. 9,421,088, which is a continuation of U.S. application Ser. No. 14/828,083, filed Aug. 17, 2015, entitled "MODULAR INTRAOCULAR LENS DESIGNS, TOOLS AND METHODS," now U.S. Pat. No. 9,364,316, which claims the benefits under 35 U.S.C. § 119(e) of priority to U.S. Provisional Patent Application No. 62/110,241, filed Jan. 30, 2015, entitled "MODULAR INTRAOCULAR LENS DESIGNS, TOOLS AND METHODS," each of which is incorporated herein by reference. This application is related to U.S. patent application Ser. No. 15/176,582, filed Jun. 8, 2016, entitled "MODULAR INTRAOCULAR LENS DESIGNS AND METHODS," now U.S. Pat. No. 9,877,825. This application also is related to U.S. patent application Ser. No. 15/054,915, filed Feb. 26, 2016, entitled "MODULAR INTRAOCULAR LENS DESIGNS AND METHODS," now U.S. Pat. No. 9,681,946. This application also is related to U.S. patent application Ser. No. 14/808,022, filed Jul. 24, 2015, entitled "MODULAR INTRAOCULAR LENS DESIGNS AND METHODS," now U.S. Pat. No. 9,387,069, which is incorporated herein by reference. This application also is related to U.S. patent application Ser. No. 14/610,360, filed Jan. 30, 2015, entitled "MODULAR INTRAOCULAR LENS DESIGNS, TOOLS AND METHODS," which claims the benefits under 35 U.S.C. § 119(e) of priority to U.S. Provisional Patent Application No. 61/941,167, filed Feb. 18, 2014, entitled "MODULAR INTRAOCULAR LENS DESIGNS, TOOLS AND METHODS," each of which is incorporated herein by reference. This application also is related to U.S. patent application Ser. No. 13/969,115, filed Aug. 16, 2013, entitled "MODULAR INTRAOCULAR LENS DESIGNS & METHODS," now U.S. Pat. No. 9,289,287, which claims the benefits under 35 U.S.C. § 119(e) of priority to U.S. Provisional Patent Application No. 61/830,491, filed Jun. 3, 2013, entitled "MODULAR INTRAOCULAR LENS DESIGNS AND METHODS," each of which is incorporated herein by reference. This application also is related to U.S. patent application Ser. No. 13/937,761, filed Jul. 9, 2013, entitled "MODULAR INTRAOCULAR LENS DESIGNS AND METHODS," now U.S. Pat. No. 9,125,736, which is incorporated herein by reference. This application also is related to U.S. patent application Ser. No. 13/748,207, filed Jan. 23, 2013, entitled "MODULAR INTRAOCULAR LENS DESIGNS & METHODS," now U.S. Pat. No. 9,095,424, which claims the benefits under 35 U.S.C. § 119(e) of priority of U.S. Provisional Patent Application No. 61/589,981, filed on Jan. 24, 2012, entitled "LASER ETCHING OF IN SITU INTRAOCULAR LENS AND SUCCESSIVE SECONDARY LENS IMPLANTATION," and of U.S. Provisional Patent Application No. 61/677,213, filed on Jul. 30, 2012, entitled "MODULAR INTRAOCULAR LENS DESIGNS & METHODS," each of which is incorporated herein by reference.

TECHNICAL FIELD

The present disclosure generally relates to intraocular lenses (IDLs). More specifically, the present disclosure relates to embodiments of modular IOL designs, methods and associated tools.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent (e.g., cloudy), vision deteriorates because of the diminished light, which can be transmitted to the retina. This deficiency in the lens of the eye is medically known as a cataract. An accepted treatment for this condition is surgical removal of the lens from the capsular bag and placement of an artificial intraocular lens (IOL) in the capsular bag. In the United States, the majority of cataractous lenses are removed by a surgical technique called phacoemulsification. During this procedure, an opening (capsulorhexis) is made in the anterior side of the capsular bag and a thin phacoemulsification-cutting tip is inserted into the diseased lens and vibrated ultrasonically. The vibrating cutting tip liquefies or emulsifies the lens so that the lens may be aspirated out of the capsular bag. The diseased lens, once removed, is replaced by an IOL.

After cataract surgery to implant an IOL, the optical result may be suboptimal or may need adjustment over time. For example, shortly after the procedure, it may be determined that the refractive correction is erroneous leading to what is sometimes called "refractive surprise." Also for example, long after the procedure, it may be determined that the patient needs or desires a different correction, such as a stronger refractive correction, an astigmatism correction, or a multifocal correction.

In each of these cases, a surgeon may be reluctant to attempt removal of the suboptimal IOL from the capsular bag and replacement with a new IOL. In general, manipulation of the capsular bag to remove an IOL risks damage to the capsular bag including posterior rupture. This risk increases over time as the capsular bag collapses around the IOL and tissue ingrowth surrounds the haptics of the IOL. Thus, it would be desirable to be able to correct or modify the optical result without the need to remove the IOL or manipulate the capsular bag.

Thus, there remains a need for an IOL system and method that allows for correction or modification of the optical result using a lens that can be attached to a base or primary lens without the need to manipulate the capsular bag.

SUMMARY OF THE DISCLOSURE

Embodiments of the present disclosure provide a modular IOL system including intraocular base and optic components, which, when combined, form a modular IOL. In general, the modular IOL allows for the lens to be adjusted or exchanged while leaving the base in place, either intraoperatively or post-operatively.

In one embodiment, a modular IOL system includes an annular base having two radially outward extending haptics. The base defines a center hole and an inside perimeter, with a radially inward open recess around the inside perimeter.

The modular IOL system also includes a lens having an optical body with first and second tabs extending radially outward from the optical body. The base and lens may be assembled with the first and second tabs of the lens disposed in the recess of the base. The first tab may be an actuatable spring, and the second tab may be a non-actuatable extension. The first tab may require radial compression for assembly of the lens with the base. The first tab may comprise a pair of cantilever springs, each with one end attached the optical body and one end free.

Drug delivery capabilities and/or sensing capabilities may be incorporated into the base, which offers several advantages over incorporating such capabilities into the lens. For example, it avoids any interference the drugs or sensors may have with the optical performance of the lens.

Embodiments of the present disclosure also provide injector devices that facilitate series or parallel delivery of the base and lens of the modular IOL. The injector may include a barrel having at least one internal lumen with at least one plunger disposed therein. After the base and the lens are both loaded into the barrel, the distal end of the barrel is placed into the eye and the plunger is advanced in the barrel to place the base and the lens into the eye. The base and the lens may be placed into the eye sequentially or simultaneously. The barrel may include a single internal lumen with a single plunger disposed therein, two side-by-side internal lumens that merge distally with a plunger disposed in each lumen, or a single internal lumen with a pair of co-axial plungers disposed therein, for example. The base and lens may be placed in the barrel in-line or side-by-side, using cartridges if desired.

The modular IOL systems, tools and methods according to embodiments of the present disclosure may be applied to a variety of IOL types, including fixed monofocal, multifocal, toric, accommodative, and combinations thereof. In addition, the modular IOL systems, tools and methods according to embodiments of the present disclosure may be used to treat, for example: cataracts, large optical errors in myopic (near-sighted), hyperopic (far-sighted), and astigmatic eyes, ectopia lentis, aphakia, pseudophakia, and nuclear sclerosis.

Various other aspects of embodiments of the present disclosure are described in the following detailed description and drawings.

BRIEF DESCRIPTION OF THE DRAWINGS

The drawings illustrate example embodiments of the present disclosure. The drawings are not necessarily to scale, may include similar elements that are numbered the same, and may include dimensions (in millimeters) and angles (in degrees) by way of example, not necessarily limitation. In the drawings:

FIGS. 6A-6C are various views of another alternative base portion of a modular IOL according to the present disclosure;

DETAILED DESCRIPTION

Figure 1:
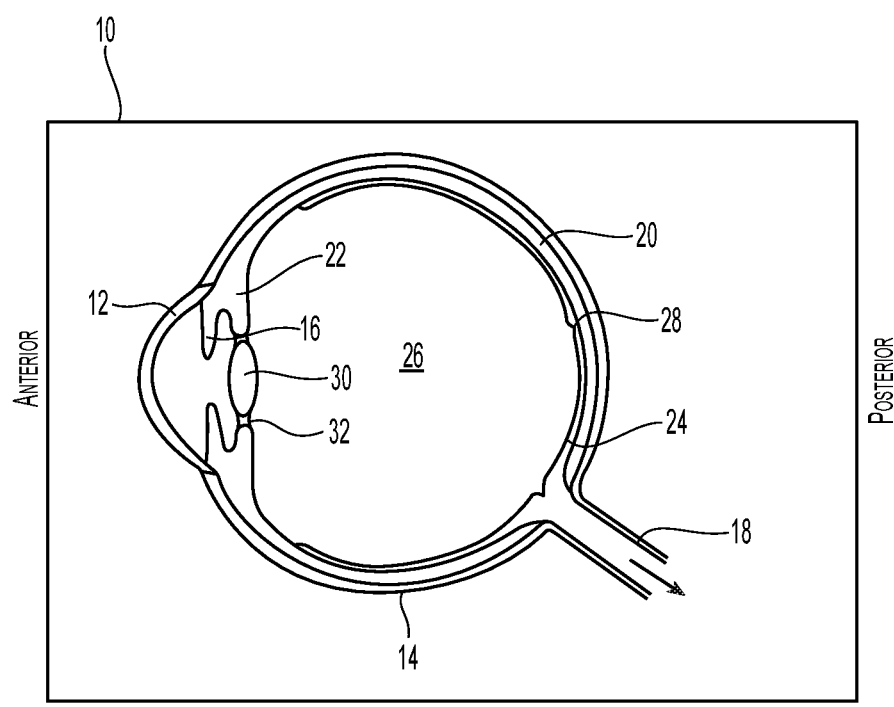
FIG. 1 is a schematic diagram of the human eye shown in cross section.

With reference to FIG. 1, the human eye 10 is shown in cross section. The eye 10 has been described as an organ that reacts to light for several purposes. As a conscious sense organ, the eye allows vision. Rod and cone cells in the retina 24 allow conscious light perception and vision including color differentiation and the perception of depth. In addition, the human eye's non-image-forming photosensitive ganglion cells in the retina 24 receive light signals which affect adjustment of the size of the pupil, regulation and suppression of the hormone melatonin, and entrainment of the body clock.

The eye 10 is not properly a sphere; rather it is a fused two-piece unit. The smaller frontal unit, more curved, called the cornea 12 is linked to the larger unit called the sclera 14. The corneal segment 12 is typically about 8 mm (0.3 in) in radius. The sclera 14 constitutes the remaining five-sixths; its radius is typically about 12 mm. The cornea 12 and sclera 14 are connected by a ring called the limbus. The iris 16, the color of the eye, and its black center, the pupil, are seen instead of the cornea 12 due to the cornea's 12 transparency. To see inside the eye 10, an ophthalmoscope is needed, since light is not reflected out. The fundus (area opposite the pupil), which includes the macula 28, shows the characteristic pale optic disk (papilla), where vessels entering the eye pass across and optic nerve fibers 18 depart the globe.

Thus, the eye 10 is made up of three coats, enclosing three transparent structures. The outermost layer is composed of the cornea 12 and sclera 14. The middle layer consists of the choroid 20, ciliary body 22, and iris 16. The innermost layer is the retina 24, which gets its circulation from the vessels of the choroid 20 as well as the retinal vessels, which can be seen within an ophthalmoscope. Within these coats are the aqueous humor, the vitreous body 26, and the flexible lens 30. The aqueous humor is a clear fluid that is contained in two areas: the anterior chamber between the cornea 12 and the iris 16 and the exposed area of the lens 30; and the posterior chamber, between the iris 16 and the lens 30. The lens 30 is suspended to the ciliary body 22 by the suspensory ciliary ligament 32 (Zonule of Zinn), made up of fine transparent fibers. The vitreous body 26 is a clear jelly that is much larger than the aqueous humor.

The crystalline lens 30 is a transparent, biconvex structure in the eye that, along with the cornea 12, helps to refract light to be focused on the retina 24. The lens 30, by changing its shape, functions to change the focal distance of the eye so that it can focus on objects at various distances, thus allowing a sharp real image of the object of interest to be formed on the retina 24. This adjustment of the lens 30 is known as accommodation, and is similar to the focusing of a photographic camera via movement of its lenses.

The lens has three main parts: the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are found predominantly on the anterior side of the lens but extend posteriorly just beyond the equator.

The lens capsule is a smooth, transparent basement membrane that completely surrounds the lens. The capsule is elastic and is composed of collagen. It is synthesized by the lens epithelium and its main components are Type IV collagen and sulfated glycosaminoglycans (GAGs). The capsule is very elastic and so causes the lens to assume a more globular shape when not under the tension of the zonular fibers, which connect the lens capsule to the ciliary body 22. The capsule varies between approximately 2-28 micrometers in thickness, being thickest near the equator and thinnest near the posterior pole. The lens capsule may be involved with the higher anterior curvature than posterior of the lens.

Various diseases and disorders of the lens 30 may be treated with an IOL. By way of example, not necessarily limitation, a modular IOL according to embodiments of the present disclosure may be used to treat cataracts, large optical errors in myopic (near-sighted), hyperopic (far-sighted), and astigmatic eyes, ectopia lentis, aphakia, pseudophakia, and nuclear sclerosis. However, for purposes of description, the modular IOL embodiments of the present disclosure are described with reference to cataracts.

The following detailed description describes various embodiments of a modular IOL system including primary and secondary intraocular components, namely an intraocular base configured to releasably receive an intraocular optic. Features described with reference to any one embodiment may be applied to and incorporated into other embodiments.

Figure 2A:
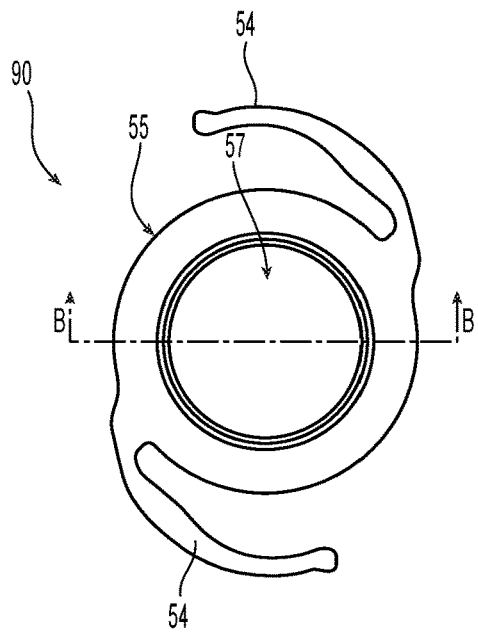
FIGS. 2A-2F are various views of a modular IOL according to the present disclosure.
Figure 2B:
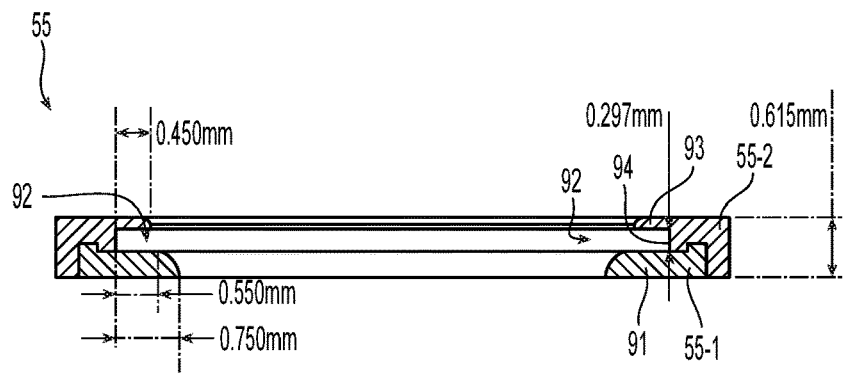
Figure 2C:
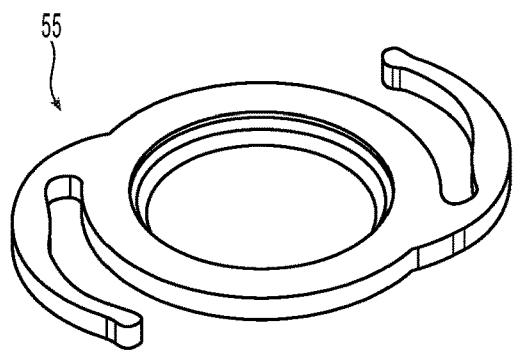
Figure 2D:
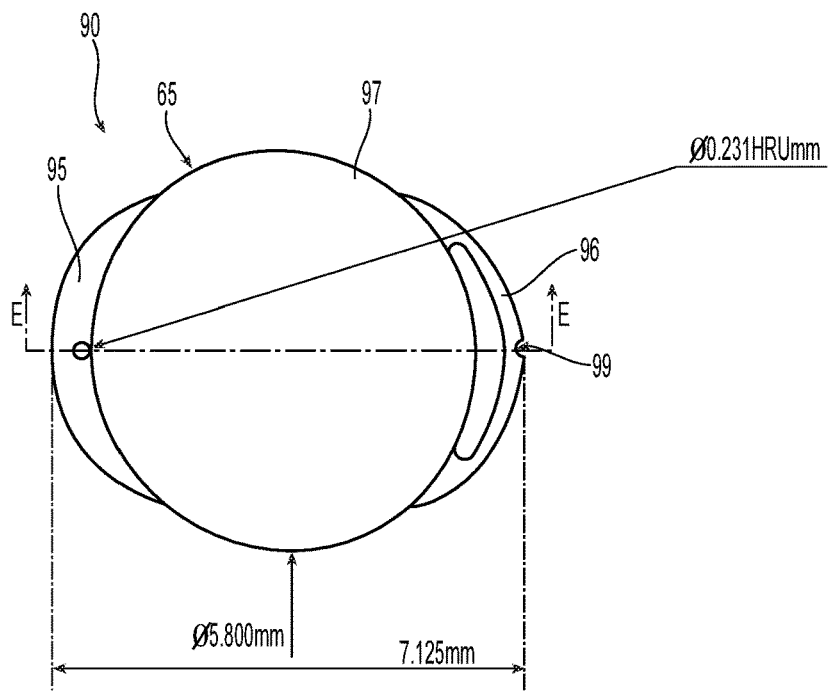
Figure 2E:
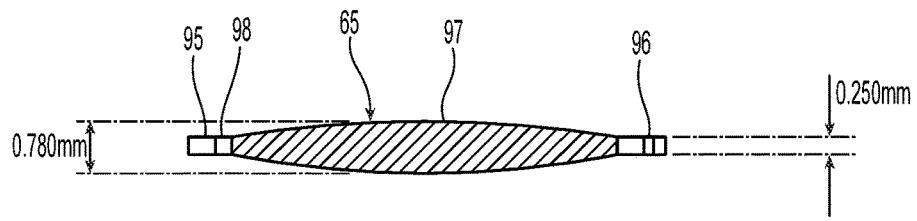
Figure 2F:
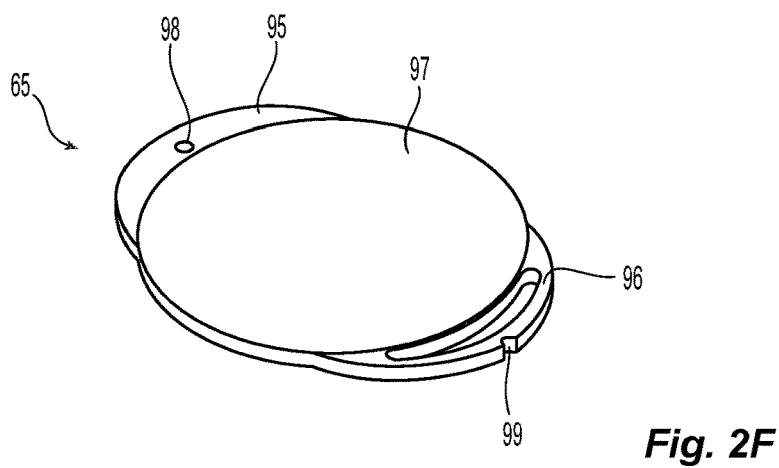

With reference to FIGS. 2A-2F, an embodiment of a modular IOL 90, comprising a base 55 and a lens 65, is shown schematically. FIGS. 2A-2C show the base portion 55 of the modular IOL 90, and FIGS. 2D-2F show the optic or lens portion 65 of the modular IOL 90. Specifically, FIG. 2A shows a front view of the base 55, FIG. 2B shows a cross-sectional view taken along line B-B in FIG. 2A, and FIG. 2C shows a perspective view of the base 55. FIG. 2D shows a front view of the lens 65, FIG. 2E shows a cross-sectional view taken along line E-E in FIG. 2D, and FIG. 2F shows a perspective view of the lens 65. Modular IOL 90 may have dimensions as shown in the drawings by way of example, not necessarily limitation.

With specific reference to FIGS. 2A-2C, the base 55 portion of the modular IOL 20 includes a pair of haptics 54 and a center hole 57 such that, except for the outermost portion, the posterior optical surface of the lens 65 is not in contact with the base 55 when the lens 65 is attached to the base 55. A recessed groove 92, which is sized and configured to receive tab portions 95 and 96 of the lens 65, defines the perimeter of the hole 57.

Recessed groove 92 includes a lower rim 91, an upper rim 93 and an inward-facing lateral wall 94. The upper rim 93 may have an inside diameter that is the same as or greater than the outside diameter of the optic portion 97 of the lens 65 (excluding tabs 95 and 96) such that the lens 65 can rest inside the hole 57 of the base 55. All or a portion of the lower rim 91 may have an inside diameter that is less than the outside diameter of the lens 65 (including tabs 95 and 96) such that the lower rim 91 acts as a ledge or backstop for the lens 65 when placed in the hole 57 of the base 55. By way of example, not necessarily limitation, the upper rim 93 may have an inside diameter of about 6.0 mm, the lower rim 91 may have an inside diameter of about 5.5 mm, the optic portion 97 of lens 65 may have an outside diameter of about 5.8 mm, and the tabs 95 and 96 may have a diameter or dimension of about 7.125 mm from the apex of tab 95 to the apex of tab 96.

The lower 91 and upper 93 rims defining the groove 92 may extend continuously around all or a portion of the perimeter of the hole 57. The base 55 may be cryo-machined in two parts, including lower or posterior portion 55-1 and upper or anterior portion 55-2, that are subsequently bonded (e.g., adhesive or solvent bond), which may lend itself well to defining a continuous groove 92. To maintain chemical and mechanical property compatibility, the adhesive and the parts 55-1 and 55-2 of the base 55 may comprise the same monomeric or polymeric formulation. For example, the adhesive may be formulated from the same acrylic monomers used in making the hydrophobic acrylic parts 55-1 and 55-2 of the base 55. Alternatively, the lower 91 and upper 93 rims defining the groove 92 may extend discontinuously around all or a portion of the perimeter of the hole 57. An example of a discontinuous arrangement is alternating segments of the lower 91 and upper 93 rims, which may lend itself well to cryo-machining the base 55 in a single part. Alternative manufacturing methods well known in the art may also be employed.

Optionally, the base posterior portion 55-1 may be a solid disc, rather than an annular ring with a hole 57, thereby defining a posterior surface against which the posterior side of the lens 65 would contact. The posterior surface may be flat or curved to conform to the posterior contour of the lens 65. This may have the advantage of providing a backstop for the lens 65 thereby making delivery and positioning of the lens 65 in the base 55 easier. This may also provide the advantage of reducing the rate of posterior capsular opacification.

With specific reference to FIGS. 2D-2F, the lens 65 of the modular IOL 90 includes an optic portion 97 and one or more tabs 95 and 96. As shown, tab 95 is fixed, whereas tab 96 may be actuated. As an alternative, fixed tab 95 may be replaced with an actuatable tab (e.g., like tab 96). Fixed tab 95 may include a thru hole 98 so that a probe or similar device may be used to engage the hole 98 and manipulate the tab 95. Actuatable tab 96 may be actuated between a compressed position for delivery into the hole 57 of the base 55, and an uncompressed extended position (shown) for deployment into the groove 92 of the base 55, thus forming an interlocking connection between the base 55 and the lens 65.

The outside curvature of the fixed tab 95 may have a radius conforming to the inside radius of the groove 92. Similarly, the outside curvature of the actuatable tab 96 may have a radius that conforms to the inside radius of the groove 92 when the actuatable tab 96 is in its uncompressed extended position. This arrangement limits relative movement between the base 55 and the lens 65 once connected.

Optionally, the lens 65 may be oval or ellipsoidal, rather than circular, with the tabs 95 and 96 positioned adjacent the long axis. This arrangement would thus define a gap between the edge of the lens 65 along its short axis and the inside perimeter of the upper rim 93 of the groove 92 in the base 55. The gap may have the advantage of providing access for a probe or similar device to pry apart the lens 65 from the base 55 if separation were needed.

Actuatable tab 96 may be attached to and extend from the lens 65 at two ends with the middle portion free of the lens 65 (like a leaf spring) as shown. Alternatively, actuatable tab 96 may be attached to and extend from the lens 65 at one end with the other end free (like a cantilever spring). Other spring configurations may be employed as known in the mechanical arts.

The actuatable tab 96 may elastically deform (e.g., by application of an in-ward lateral force) to its compressed position. To facilitate low force compression, a dimple 99 may be provided on the outside (and/or inside) curvature of the tab to form a hinge in the spring.

Figure 3A:
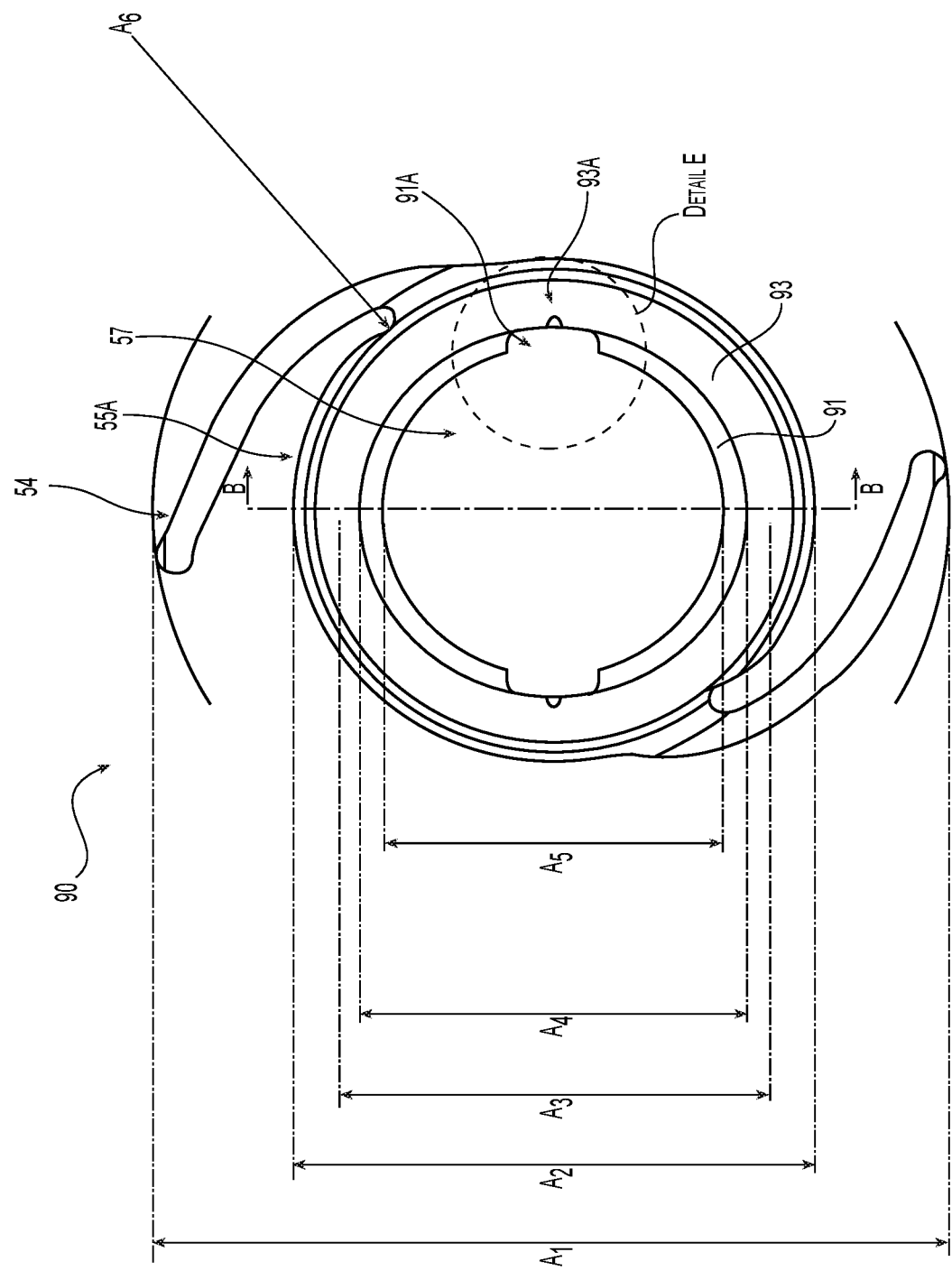
FIGS. 3A-3F are various views of an alternative base portion of a modular IOL according to the present disclosure.
Figure 3B:
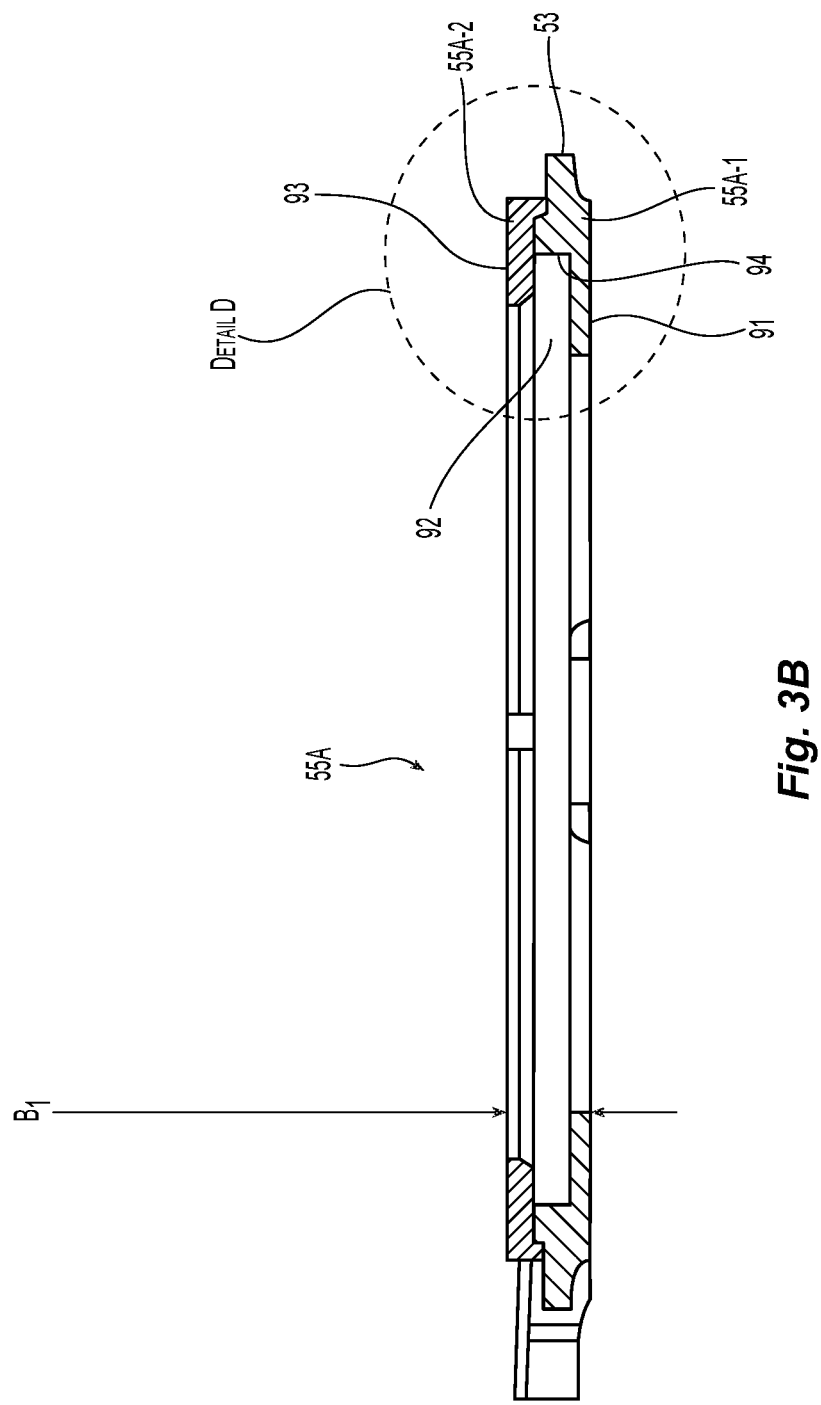
Figure 3C:
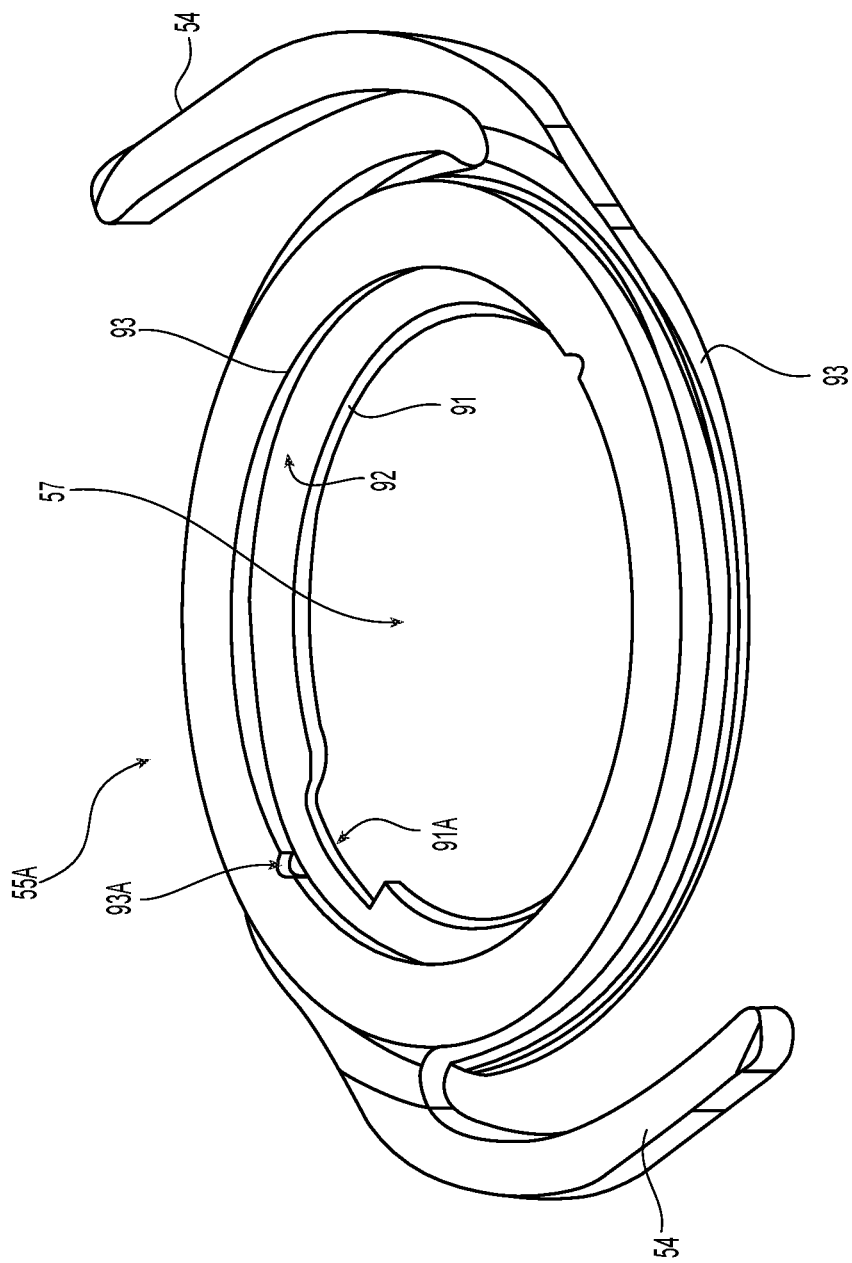
Figure 3D:
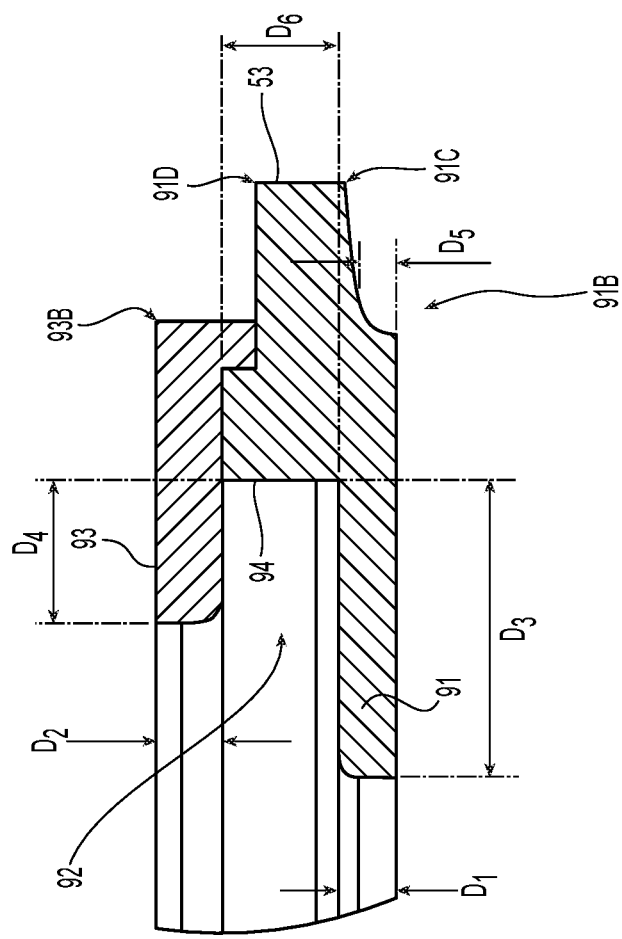
Figure 3E:
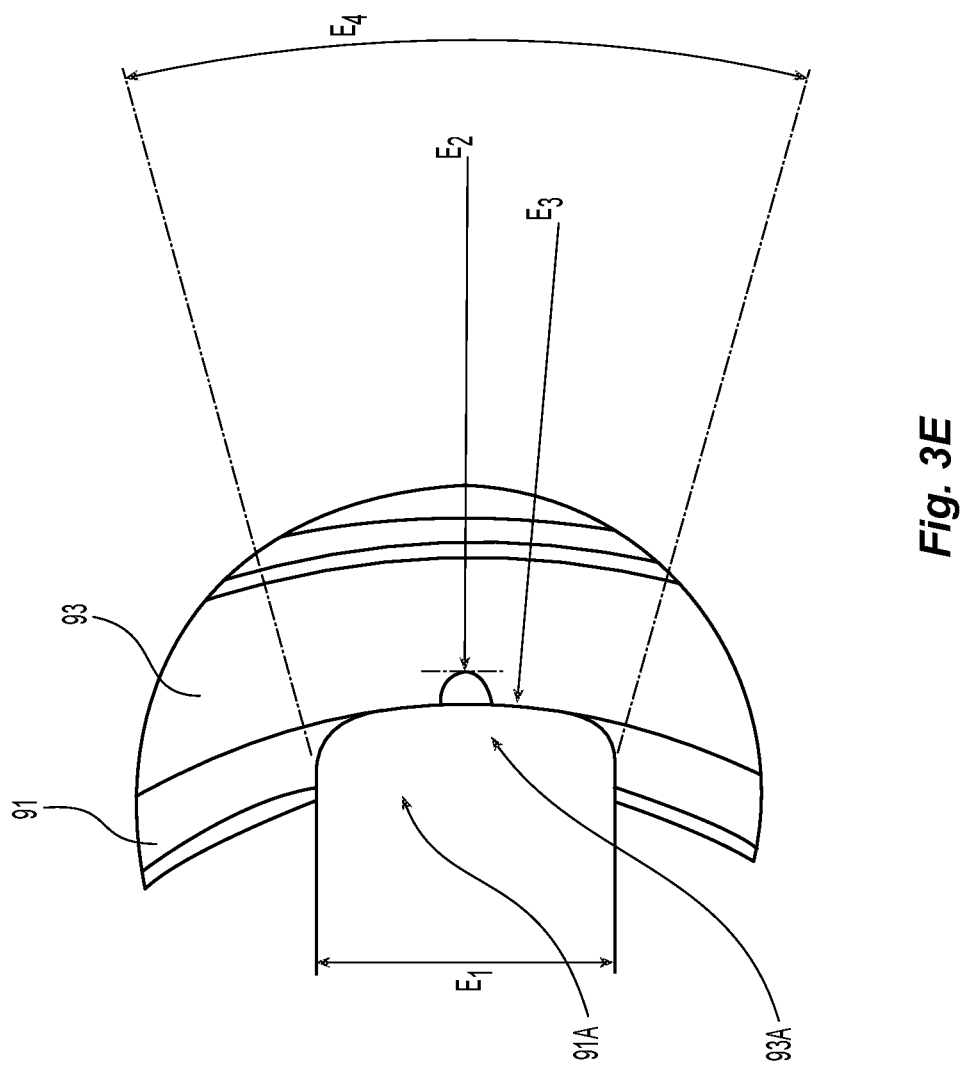
Figure 3F:
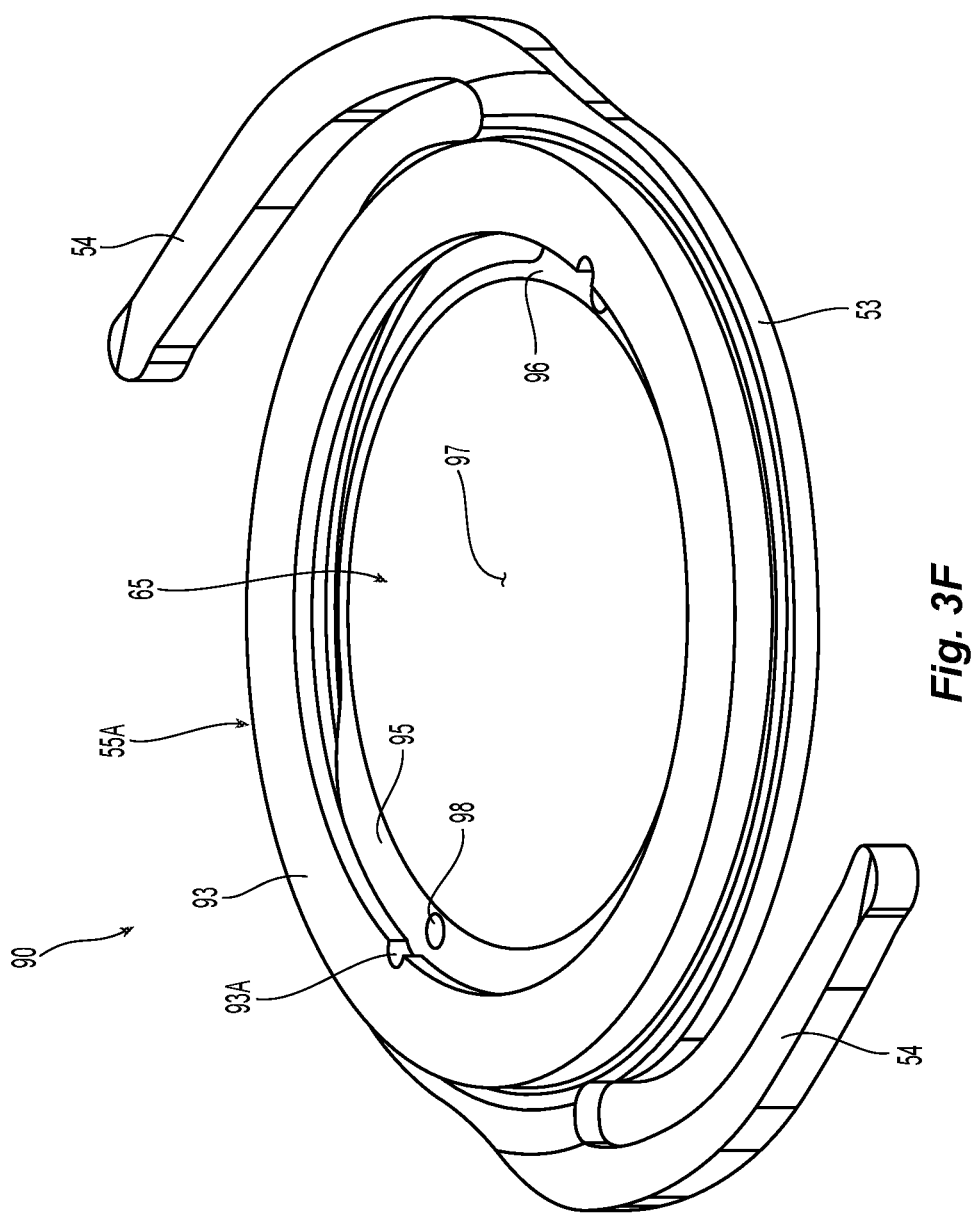

FIGS. 3A-3F show an alternative base portion 55A of the modular IOL 90. Specifically, FIG. 3A shows a front view of the base 55A, FIG. 3B shows a cross-sectional view taken along line B-B in FIG. 3A, FIG. 3C shows a perspective view of the base 55A, FIG. 3D shows a detail view of circle D in FIG. 3B, FIG. 3E shows a detail view of circle E in FIG. 3A, and FIG. 3F shows a perspective view of the assembled modular IOL 90 including base 55A and lens 65. In this alternative embodiment, all aspects of the base 55A of the modular IOL 90 are substantially the same except for the provision of a pair of cutouts 91A, a pair of notches 93A, an outer rim 53, and sharp edges 91B and 91C. All similar aspects of the prior embodiment are incorporated by reference into the description of this embodiment. Also, dimensions are provided by way of example, not necessarily limitation.

As in the prior embodiment, the base 55A portion of the modular IOL 90 in this alternative embodiment includes a pair of haptics 54 and a center hole 57 such that, except for the outermost portion, the posterior optical surface of the lens 65 is not in contact with the base 55A when the lens 65 is attached to the base 55A. Also as in the prior embodiment, the base 55A may be formed as a single piece, or formed as a posterior portion 55A-1 and an anterior portion 55A-2 that are fixed to each other by adhesive or the like (as shown). A recessed groove 92, which is sized and configured to receive tab portions 95 and 96 of the lens 65, defines the perimeter of the hole 57. The recessed groove 92 includes a lower rim 91, an upper rim 93 and an inward-facing lateral wall 94. The lower rim 91 may be part of the posterior portion 55A-1 of the base 55A, and the upper rim may be part of the anterior portion 55A-2 of the base 55A In this alternative embodiment of the base 55A of modular IOL 90, the lower rim 91 may include one or more cutouts 91A, which aid in removing visco-elastic intra-operatively. Also in this alternative embodiment, the upper rim 93 may include one or more notches 93A to provide access for a Sinskey hook intra-operatively, which allows the base 55A to be more easily manipulated.

Further in this embodiment, the base 55A may include an outer rim 53 extending around substantially the entire periphery of the base 55A. The outer rim 53 may be formed as a part of the posterior portion 55A-1 of the base 55A as shown, or as a part of the anterior portion 55A-2 of the base. At the junction of the haptic 54, the outer rim 53 may terminate short of the inside curvature of the haptic 54 to provide a flexible junction of the haptic 54 to the body of the base 55A, and the outer rim 53 may extend continuously with the outside curvature of the haptic 54.

The posterior-most side of base 55A may include at least one corner edge 91B along its perimeter, and the outside perimeter of the body of the base 55A may include corner edges 91C and 91D, all to reduce the tendency for posterior capsular opacification. In addition, an anterior corner edge 93B may be formed along the anterior perimeter of the base 55A. The corner edges 91B, 91C and 91D may be formed into the posterior portion 55A-1 of the base 55A defining lower rim 91, and the corner edge 93B may be formed into the anterior portion 55A-2 of the base 55A defining upper rim 93. In cross-section, the corner edges 91B, 91C, 91D and 93B may be defined by a square angle, an acute angle, or an obtuse angle. The posterior corner edge 91B may be flush with the posterior surface as shown, or may protrude posteriorly. The base 55A may be machined without subsequent tumbling to better form the corner edges 91B, 91C, 91D and 93B. Preferably, the corner edges 91B, 91C, 91D and 93B may extend around the entire circumference of the base 55A.

Note with reference to FIGS. 2B, 3B and 2E that the lower rim 91 and the upper rim 93 may define an anterior-posterior (AP) dimension around the perimeter of the base 55/55A that is greater than the corresponding AP dimension of the lens 65 adjacent the tabs 95 and 96 that fit into groove 92. For example, the AP dimension of the perimeter of the base 55/55A may be 0.615 mm as shown in FIGS. 2B and 3B, and the corresponding AP dimension of the lens 65 adjacent the tabs 95, 96 may be 0.25 mm as shown in FIG. 2E. When the modular IOL 90 is implanted in the capsular bag, these relative dimensions provide a standoff between the posterior capsule and the posterior side of the lens 65, as well as a standoff between the anterior capsule adjacent the capsulorhexis (sometimes call anterior leaflets) and the anterior side of the optic. This standoff reduces the likelihood of cellular proliferation and the potential for resulting opacification of the lens 65 and/or tissue adhesion to the lens 65 that might otherwise interfere with post-operative optic exchange. Because such cellular proliferation typically grows radially inward, the standoff may be provided adjacent the perimeter of the lens 65 adjacent the inside circumference of the lower and upper rims 91, 93, whereas the center of the optic may or may not have a standoff, with an AP dimension that is less than, the same as or greater than the AP dimension around the perimeter of the base 55/55A. For example, the center of the optic may have an AP dimension of 0.78 mm as shown in FIG. 2E (depending on the diopter), which is greater than the AP dimension of the perimeter of the base 55/55A at 0.615 mm as shown in FIGS. 2B and 3B. Additionally, the lower (posterior) rim 91 may have a greater AP dimension than the upper (anterior) rim 93 recognizing the cellular proliferation may be more likely on the posterior side than the anterior side due to the presence of the capsulorhexis on the anterior side and the corresponding lower tissue contact area on the anterior side. Those skilled in the art will recognize the importance of the relative dimensions to achieve this effect rather than the specific dimensions, which are provided by way of example, not necessarily limitation.

By way of example, not necessarily limitation, the following dimensions are provided with reference to alternative base 55A illustrated in FIGS. 3A-3E. In FIG. 3A, diameter A1 may be 13.00±0.02 mm, diameter A2 may be 8.50±0.10 mm, diameter A3 may be 7.00±0.051 mm, diameter A4 may be 6.30±0.051 mm, diameter A5 may be 5.50+0.15/−0.05 mm, and diameter A6 may be 7.92 mm. In FIG. 3B, dimension B1 may be 0.615±0.020 mm. In FIG. 3D, dimension D1 may be 0.15 mm, dimension D2 may be 0.17 mm, dimension D3 may be 0.75 mm, dimension D4 may be 0.35 mm, dimension D5 may be 0.08 mm, and dimension D6 may be 0.30±0.02 mm. In FIG. 3E, dimension E1 (width of cutouts 91A) may be 1.48 mm, dimension E2 (diameter at outer edge of notches 93A) may be 6.62 mm, dimension E3 (inside diameter of upper rim 93) may be 6.25 mm, and dimension E4 (radian of cutouts 91A) may be 30 degrees.

In general, the modular IOL 90 allows for the lens 65 to be adjusted or exchanged while leaving the base 55 in place, either intra-operatively or post-operatively. Examples of instances where this may be desirable include, without limitation: exchanging the lens 65 for a suboptimal refractive result detected intra-operatively; exchanging the lens 65 for a suboptimal refractive result detected post-operatively (residual refractive error); rotationally adjusting the lens 65 relative to the base 55 to fine tune toric correction; laterally adjusting the lens 65 relative to the base 55 for alignment of the optic with the true optical axis (which may not be the center of the capsular bag); and exchanging the lens 65 for the changing optical needs or desires of the patient over longer periods of time. Examples of the latter instance include, but are not limited to: an adult or pediatric IOL patient whose original optical correction needs to be changed as s/he matures; a patient who wants to upgrade from a monofocal IOL to a premium IOL (toric, multifocal, accommodating or other future lens technology); a patient who is not satisfied with their premium IOL and wants to downgrade to monofocal IOL; and a patient who develops a medical condition where an IOL or a particular type of IOL is contra-indicated.

An example of how the modular IOL 90, including base 55 and lens 65, may be implanted is shown in FIGS. 4A-4D. An example of how the lens 65 may be removed from the base 55 is shown in FIGS. 4E-4G. After the lens 65 is removed from the base 55 (and the eye), a different lens 65 may be implanted in the same base 55 following the steps described with reference to FIGS. 4C-4D.

Figure 4A:
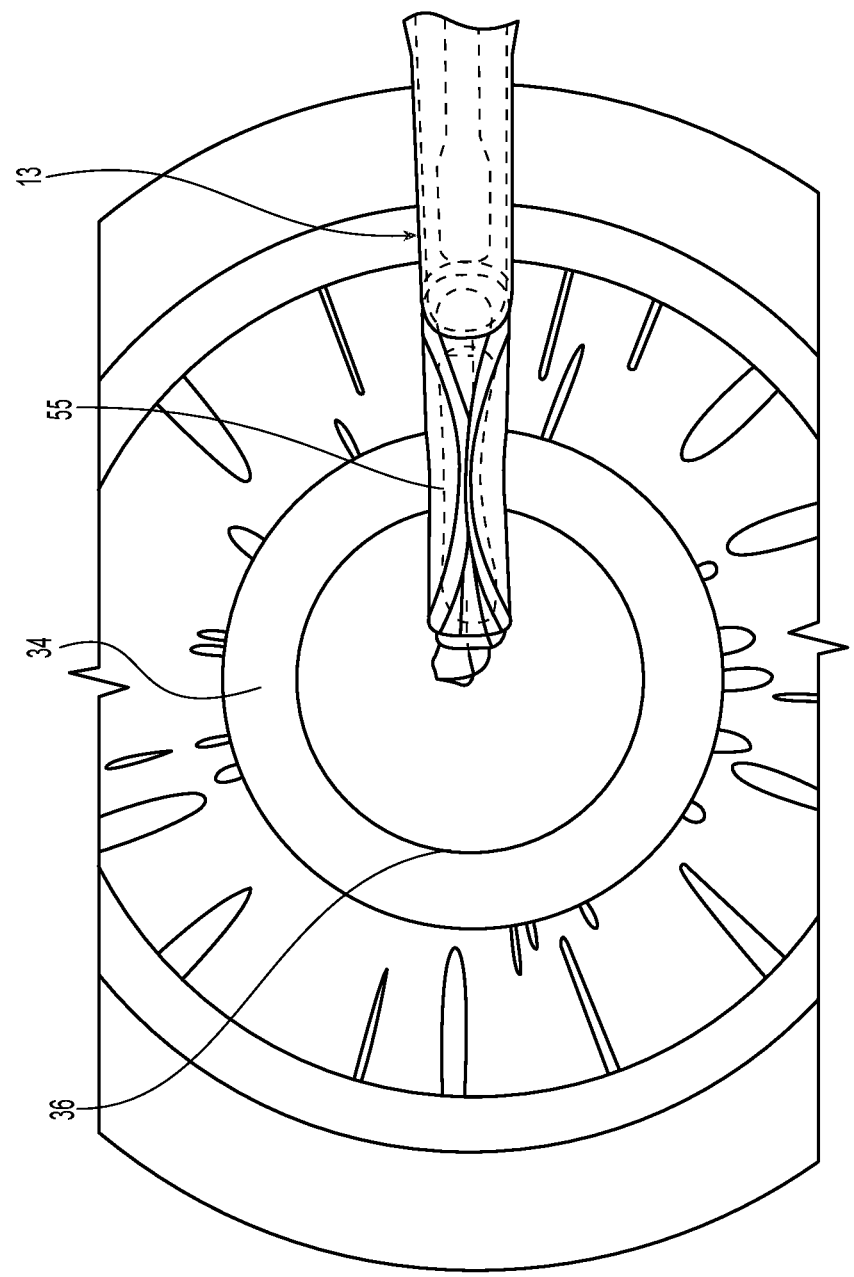
FIGS. 4A-4G show an example method of how a modular IOL may be implanted and removed.
Figure 4B:
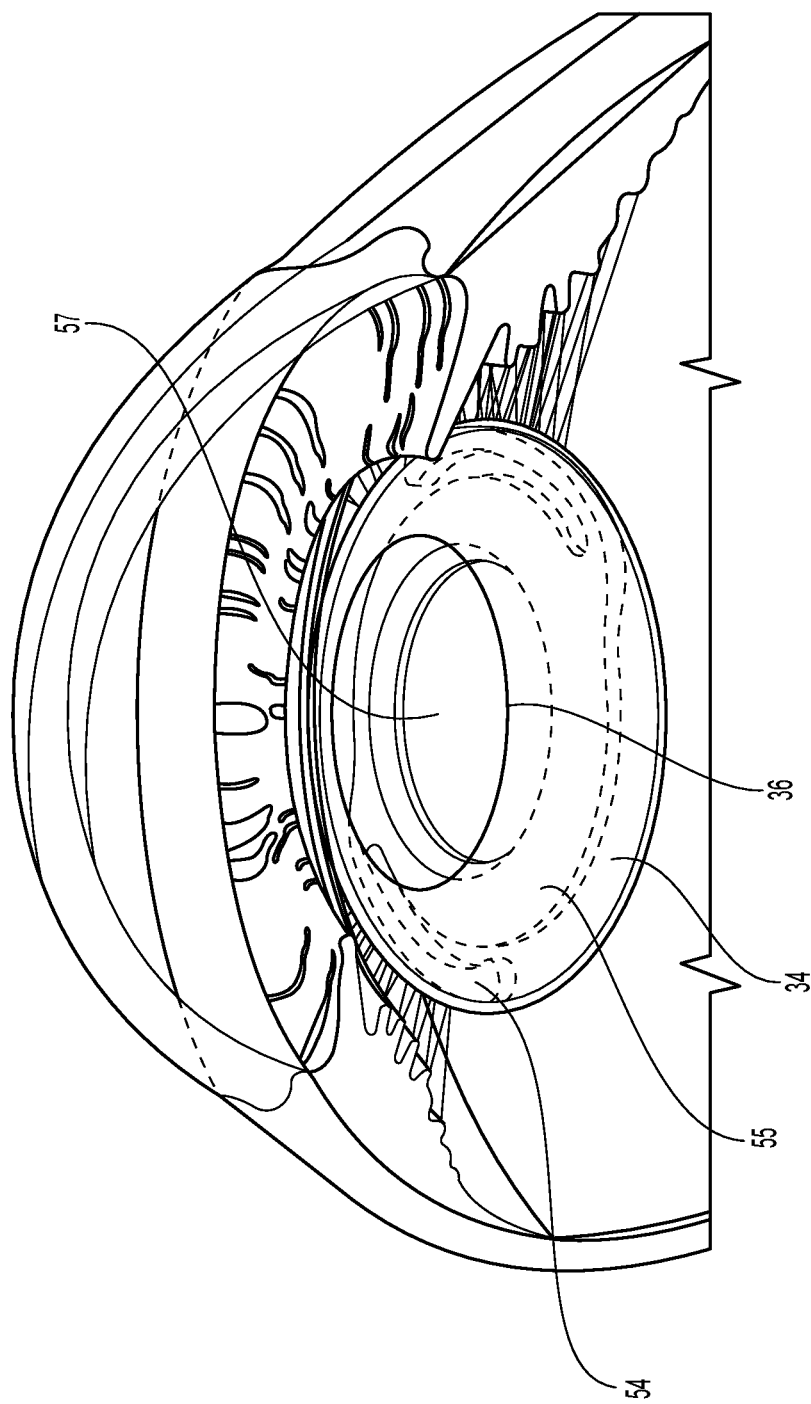

As shown in FIG. 4A, the modular IOL 90 may be implanted by initially delivering the base 55 into the capsular bag in a rolled configuration using an injector (a.k.a., inserter or delivery tube) inserted through a corneal incision 13, through the capsulorhexis 36, and into the capsular bag 34. As shown in FIG. 4B, the base 55 may be ejected from the injector and allowed to unfurl. With gentle manipulation, the haptics 54 of the base 55 engage the inside equator of the lens capsule 34 and center the hole 57 of the base 55 relative to the capsulorhexis 36.

The lens 65 may also be delivered in a rolled configuration using an injector, positioning the distal tip thereof adjacent the base 55. The lens 65 may be ejected from the injector and allowed to unfurl. With gentle manipulation, the lens 65 is centered relative to the capsulorhexis 36. Once the base 55 has been delivered and unfurled in the capsular bag, the lens 65 may be connected to the base 55 via placing tabs 95 and 96 into groove 92 to provide an interlocking connection between the base 55 and the lens 65.

Figure 4C:
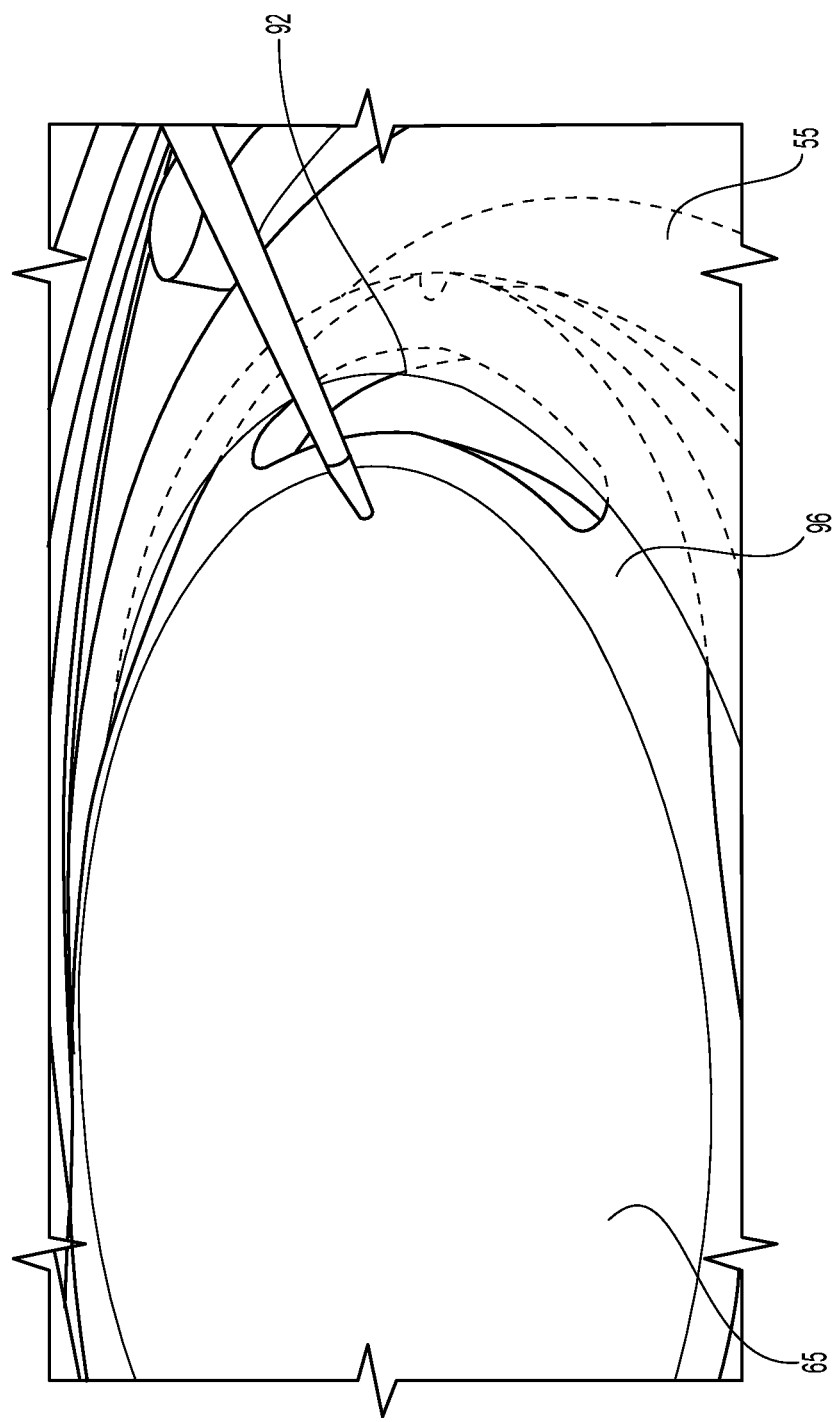
Figure 4D:
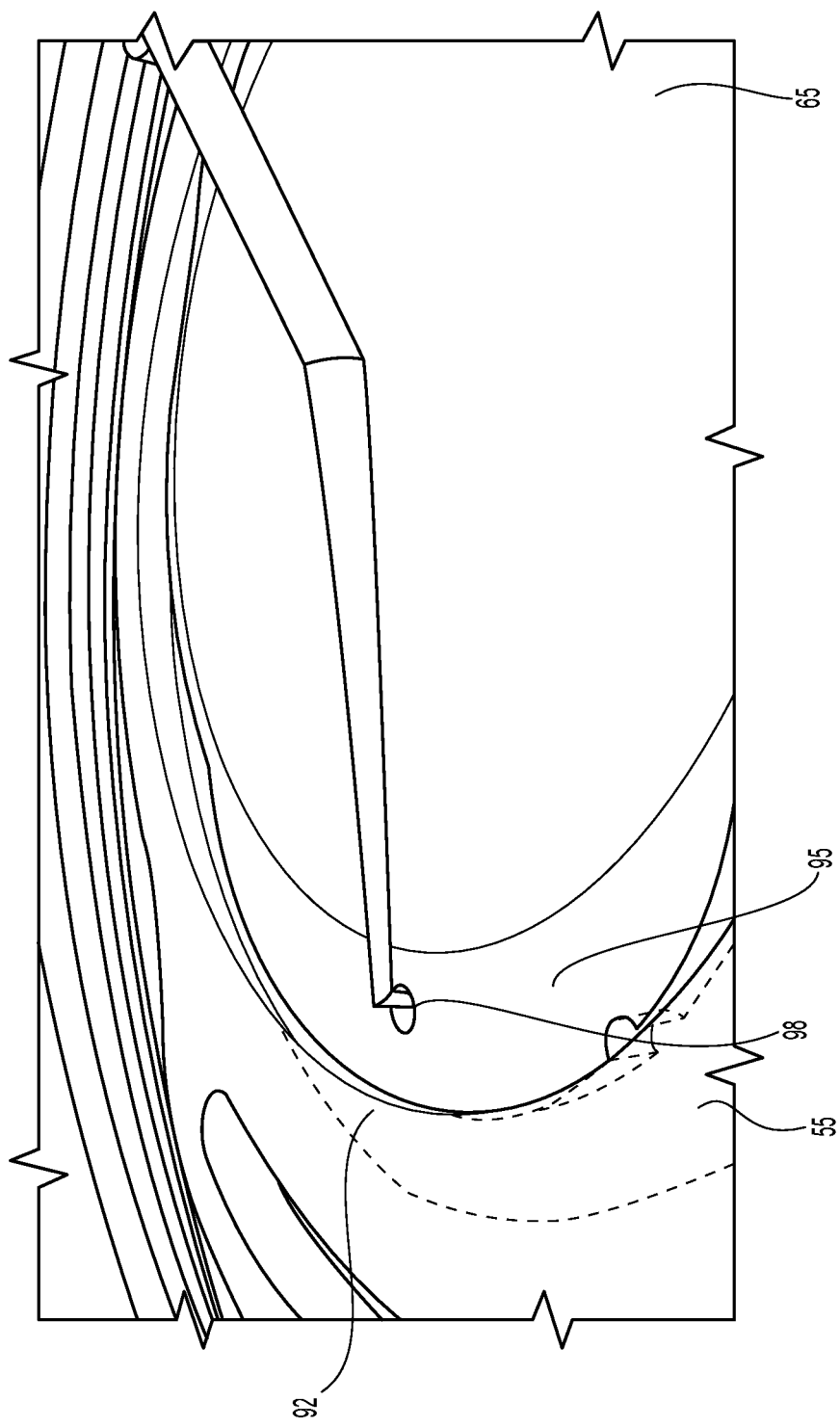
Figure 4E:
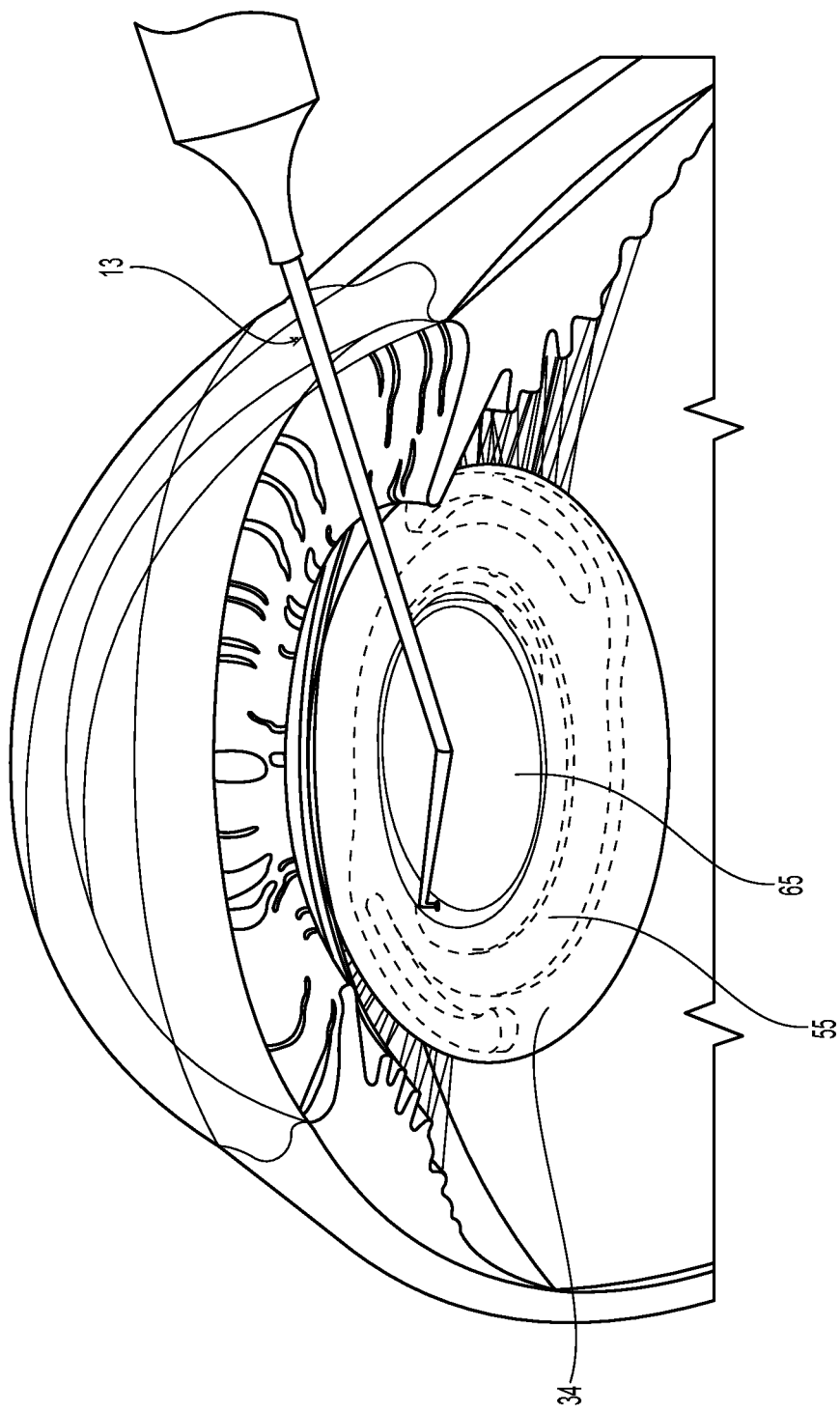
Figure 4F:
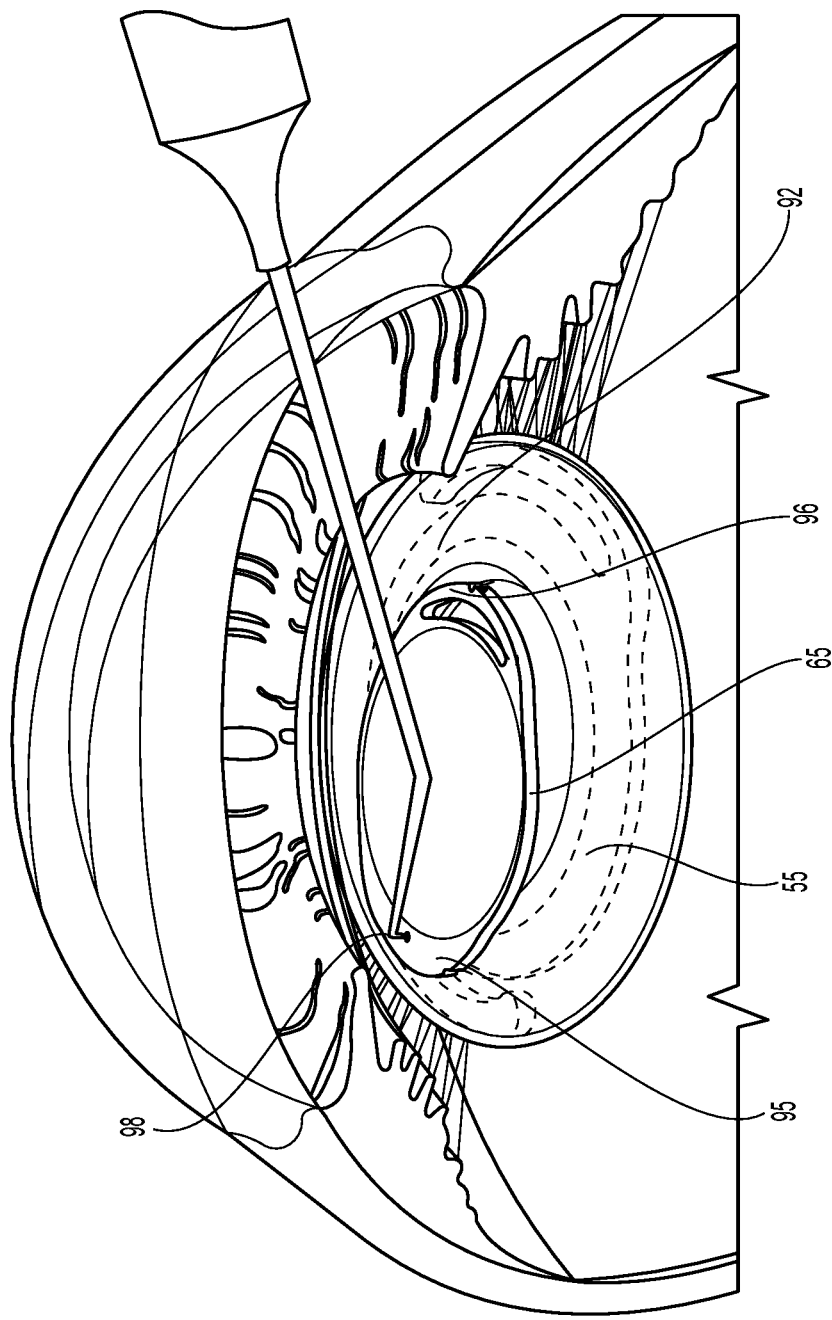
Figure 4G:
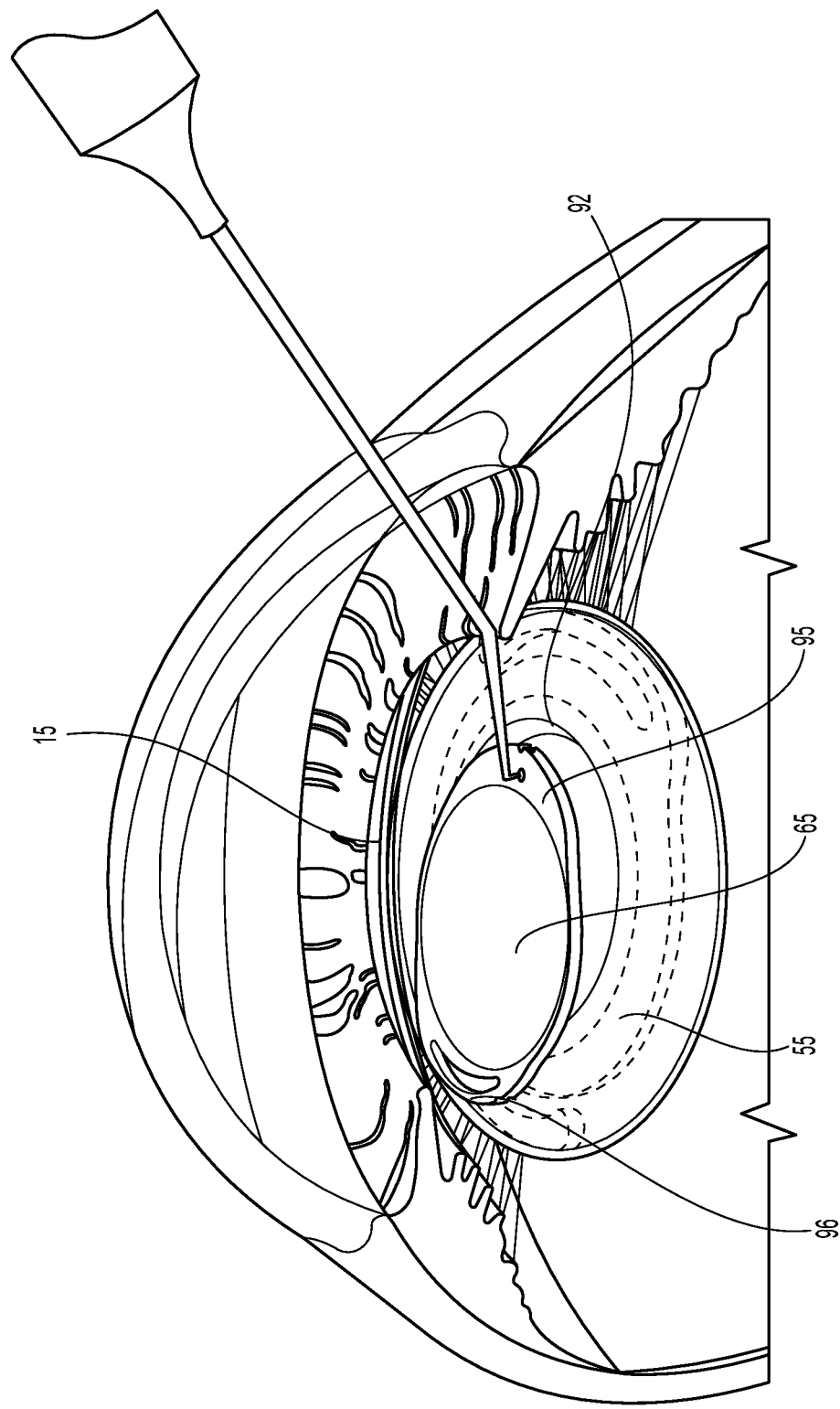

As shown in FIGS. 4C-4D, the lens 65 may be connected to the base 55 by first inserting the actuatable tab 96 into the groove 92. The actuatable tab 96 may then be compressed by application of a lateral force using a probe or similar device inserted into hole 98 of fixed tab 95, allowing the lens 65 to be advanced into the hole 57 of the base 55 such that the lens 65 and base 55 are coplanar.

The compressive force may then be released from the actuatable tab 96, allowing the fixed tab 95 to slide into the groove 92 of the base 55, thus connecting the lens 65 to the base 55. By using a lateral force to compress the interlocking feature rather than an anterior-posterior force, the risk of posterior rupture of the capsular bag is reduced. The probe may be removed from hole 98. Reverse steps may be followed to disconnect the lens 65 from the base 55.

The actuatable tab 96 and groove 92 may be described as interlocking members that provide an interlocking connection between the base 55 and the lens 65, wherein at least one of the pair of interlocking members is actuatable to lock or unlock the connection therebetween. More generally, one or more interlocking connections may be provided between the base and lens. Each interlocking connection may include a pair of interlocking members, wherein one or both of the interlocking members are actuatable. The actuatable interlocking member may be associated with the lens as described with reference to modular IOL 90 in FIGS. 2A-2F.

As shown in FIGS. 4E-4G, lens removal begins by disengaging a lens 65 from a base 55. As shown in FIG. 4E, a probe or similar device may pass through the corneal incision 13, capsulorhexis 36, and enter the capsular bag 34 containing a modular IOL, for example modular IOL 90. As shown in FIG. 4F, the probe or similar device may engage the hole 98 of fixed tab 95 and compress the actuatable tab 96 by application of a lateral force. Upon compression, fixed tab 95 may separate from groove 92 of the base 55. With gentle manipulation, the lens 65 may be lifted such that the lens 65 and base 55 are no longer coplanar. Once freed, the compressive force may then be released and the actuatable tab 96 may elastically expand and separate from the groove 92 of the base 55.

As shown in FIG. 4G, the probe or similar device may be used to pass the lens 65 from the capsular bag 34 into the anterior chamber 15. This step does not damage the eye or expand the size of the capsulorhexis 36 because the width of the lens 65 is less than the width of the capsulorhexis 36. The probe or similar device may also rotate the lens 65 into an orientation where the fixed tab 95 is proximal to the corneal incision 13 and the actuatable tab 96 is distal to the corneal incision 13.

A typical corneal incision 13 may have a width of about 2.2 mm, less than the outer diameter of the lens 65. Removing the lens 65 from the anterior chamber 15 through the corneal incision 13 may thus require mechanical manipulation of the lens 65. The lens 65 may be manipulated, for example cut, such that it can be pulled through the corneal incision, either as a single piece or in multiple pieces. A cannula or tube may be used to facilitate this removal.

A conventional injector (a.k.a., inserter) may be used to deliver the base 55 and lens 65. Examples of suitable injectors are described in U.S. Pat. No. 5,123,905 to Kelman, U.S. Pat. No. 4,681,102 to Bartell, U.S. Pat. No. 5,304,182 to Rheinish, and U.S. Pat. No. 5,944,725 to Cicenas. Such injectors may be configured to deliver the base 55 and lens 65 singly as described with reference to FIGS. 4A-4G. Alternatively, the base 55 and lens 65 may be loaded into an injector in-line for delivery in series (i.e., sequentially) or loaded pre-assembled for delivery in parallel (i.e., simultaneously). Examples of alternative injector configurations that facilitate series or parallel delivery are shown in FIGS. 5A-5D.

Figure 5A:
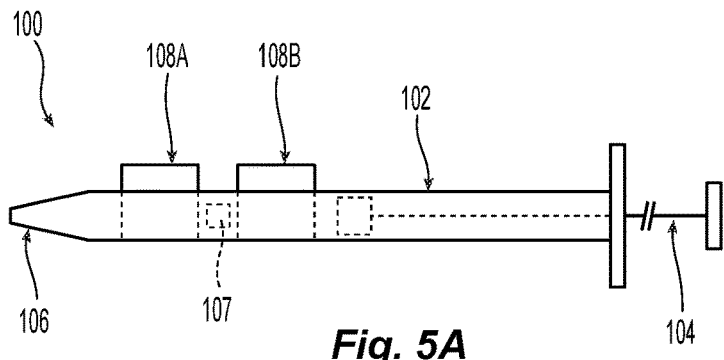
FIGS. 5A-5D are side schematic views of alternative series or parallel devices for implanting a modular IOL into the eye.

With reference to FIG. 5A, alternative injector 100 includes a tubular barrel 102 having a single internal lumen with a plunger 104 disposed therein. The distal end 106 of the barrel 102 is tapered for insertion into a corneal incision. A pair of in-line cartridges 108A and 108B are disposed in the barrel 102 and are configured to hold the base 55 and lens 65, respectively, in a rolled configuration (not visible). Cartridges 108A and 108B may be configured as disclosed in Bartell '102 mentioned above, except that two in-line cartridges are provided instead of one. As an alternative to cartridges 108A and 108B, the base 55 and lens 65 may be pre-disposed in the barrel 102 or placed in the barrel 102 through a side-load opening as described by Kelman '905 mentioned above. Optionally, a spacer 107 may be disposed between the cartridges 108A and 108B inside the barrel 102.

Upon advancement of the plunger 104 inside the barrel 102, the distal end of the plunger 104 pushes the lens 65 out of cartridge 108B which, in turn, pushes the spacer 107 (if used) to engage the base 55 disposed in cartridge 108A. Continued advancement of the plunger 104 pushes the base 55 out of the distal end 106 of the injector 100 and into the eye, followed by the lens 65. The lens 65 may then be attached to the base 55 inside the eye. The spacer 107 may be tethered to the injector to avoid implantation in the eye, or it may be formed of a dissolvable material that can be left in the eye. The base 55 may have a lower volume than lens 65 (i.e., less material) such that the force required to advance the base 55 in the barrel 102 is lower than the force required to advance the lens 65 in the barrel 102, thus reducing the tendency of the lens 65 to jam inside the barrel 102 as it pushes against the base 55.

Figure 5B:
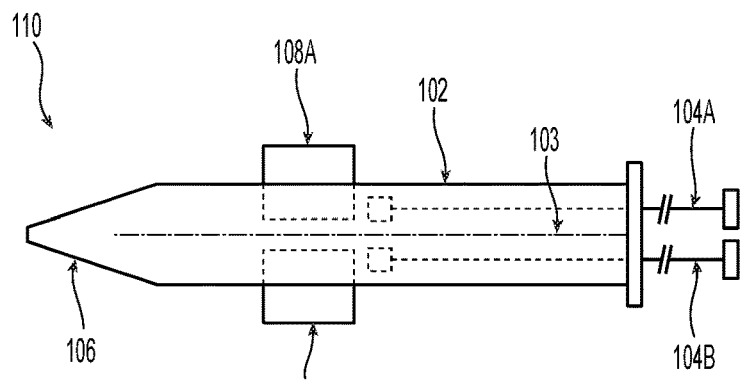

With reference to FIG. 5B, another alternative injector 110 includes a tubular barrel 102 having two side-by-side internal lumens separated by internal wall 103, with a pair of plungers 104A and 104B disposed therein. The distal end 106 of the barrel 102 includes a common single lumen where the two side-by-side lumens merge and the wall 103 terminates. The distal end 106 of the barrel 102 is tapered for insertion into a corneal incision. A pair of side-by-side cartridges 108A and 108B are disposed in the barrel 102 and are configured to hold the base 55 and lens 65, respectively, in a rolled configuration (not visible) in each of the side-by-side lumens. Cartridges 108A and 108B may be configured as disclosed in Bartell '102 mentioned above, except that two side-by-side cartridges are provided instead of one. As an alternative to cartridges 108A and 108B, the base 55 and lens 65 may be pre-disposed in the barrel 102 or placed in the barrel 102 through side-load openings as described by Kelman '905 mentioned above. Upon advancement of the plunger 104A inside the barrel 102, the distal end of the plunger 104A pushes the base 55 out of cartridge 108A, out of the distal end 106 of the injector 100 and into the eye. Plunger 104A may then be retracted into its original position. Subsequently, plunger 104B may be advanced inside the barrel 102 to push the lens 65 out of cartridge 108B, out of the distal end 106 of the injector 100 and into the eye. The lens 65 may then be attached to the base 55 inside the eye.

Figure 5C:
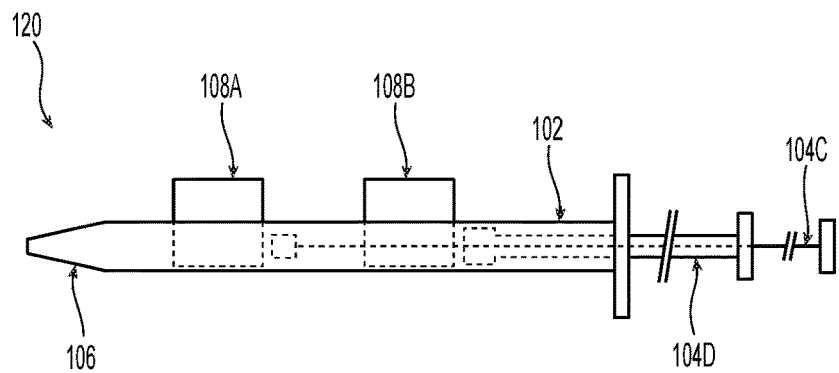

With reference to FIG. 5C, another alternative injector 120 includes a tubular barrel 102 having a single internal lumen with a pair of co-axial plungers 104C and 104D disposed therein. The inner plunger 104C is configured to be axially movable inside outer tubular plunger 104D. The distal end 106 of the barrel 102 is tapered for insertion into a corneal incision. A pair of in-line cartridges 108A and 108B are disposed in the barrel 102 and are configured to hold the base 55 and lens 65, respectively, in a rolled configuration (not visible). Cartridges 108A and 108B may be configured as disclosed in Bartell '102 mentioned above, except that two in-line cartridges are provided instead of one. As an alternative to cartridges 108A and 108B, the base 55 and lens 65 may be pre-disposed in the barrel 102 or placed in the barrel 102 through a side-load opening as described by Kelman '905 mentioned above. The lens 65 may be rolled about the shaft of the inner plunger 104C allowing the inner plunger 104C to slide therethrough. Upon advancement of the inner plunger 104C inside the outer plunger 104D and barrel 102, the distal end of the inner plunger 104C pushes the base 55 out of cartridge 108A. Continued advancement of the inner plunger 104C causes the distal end thereof to push the base 55 out of the distal end 106 of the injector 100 and into the eye. The inner plunger 104C may then be retracted to its original position. Upon subsequent advancement of the outer plunger 104D over the inner plunger 104C, the distal end of the outer plunger 104D pushes the lens 65 out of the cartridge 108B. Continued advancement of the outer plunger 104D pushes the lens 65 off the distal end of the inner plunger 104C, out of the distal end 106 of the injector 100 and into the eye. The lens 65 may then be attached to the base 55 inside the eye.

Figure 5D:
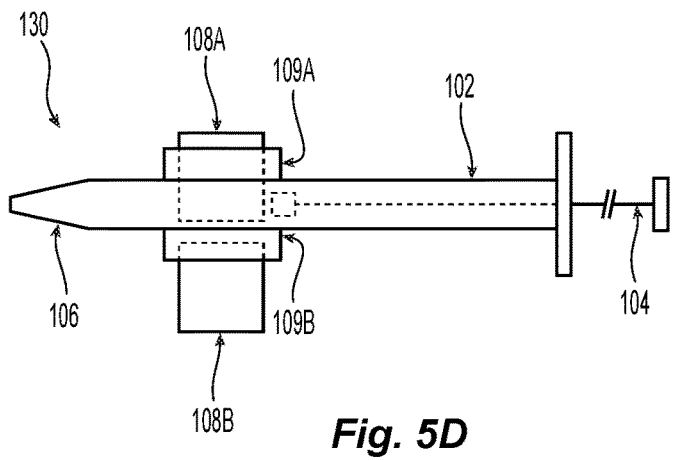

With reference to FIG. 5D, another alternative injector 130 includes a tubular barrel 102 having a single internal lumen with a plunger 104 disposed therein. The distal end 106 of the barrel 102 is tapered for insertion into a corneal incision. A pair of side-by-side cartridges 108A and 108B are disposed in lateral slot extensions 109A and 109B, respectively. Cartridges 108A and 108B and are configured to hold the base 55 and lens 65, respectively, in a rolled configuration (not visible). Cartridges 108A and 108B may be configured as disclosed in Bartell '102 mentioned above, except that two side-by-side cartridges are provided instead of one. As an alternative to cartridges 108A and 108B, the base 55 and lens 65 may be pre-disposed in the barrel 102 or placed in the barrel 102 through side-load openings as described by Kelman '905 mentioned above.

With continued reference to FIG. 5D, the side-by-side cartridges 108A and 108б slide laterally inside the slot extensions 109A and 109б to align the base 55 contained in cartridge 108A with the lumen of the barrel 102 when pushed in a first position (down position as shown), and to align the lens 65 contained in cartridge 108б with the lumen of the barrel 102 when pushed into a second position (up position, not shown). Initially, cartridge 108A containing base 55 is pushed into the slot extension 109A and into the barrel 102. Upon advancement of the plunger 104 inside the barrel 102, the distal end of the plunger 104 pushes the base 55 out of cartridge 108A, out of the distal end 106 of the injector 100 and into the eye. Plunger 104 may then be retracted into its original position (as shown). Subsequently, cartridge 108B is pushed into slot extension 109B and into the barrel 102, pushing empty cartridge 108A out of the barrel 102 and into slot extension 109A. Plunger 104 may then be advanced inside the barrel 102 to push the lens 65 out of cartridge 108б, out of the distal end 106 of the injector 100 and into the eye. The lens 65 may then be attached to the base 55 inside the eye. The cartridges 108A and 108B may be slid manually as described or may be automatically moved, for example, using a spring to bias to push cartridge 108б containing lens 65 into the barrel 102 when the plunger 104 is retracted after delivering the base 55 from cartridge 108A.

As mentioned previously, the base 55 and lens 65 may be delivered in series or in parallel. For delivery in parallel, the lens 65 may be pre-assembled with the base 55, rolled together, and then loaded into an injector for delivery into the eye, thus negating the need to assemble the two inside the eye. A dissolvable adhesive, a severable member (e.g., a tab, tether or hinge severable by cutting or laser ablating) or other temporary connecting means may be used to maintain the assembled connection between the base 55 and lens 65 during the rolling, loading and delivery process. Alternatively, the lens 65 may be stacked onto the base 55 (without assembling the two), rolled together, loaded into an injector, delivered into the eye, and then assembled inside the eye.

FIGS. 6A-6C illustrate another alternative base 55B for use with the modular IOL 90. FIG. 6A is a perspective view of the base 55B, FIG. 6B is a top (anterior) view of the base 55B, and FIG. 6C is a perspective sectional view of the base 55B taken along line C-C in FIG. 6B. Alternative base 55B is similar to base 55 except for the configuration of the groove 92 and the overall size of the base 55B. All similar aspects of the prior embodiment are incorporated by reference into the description of this embodiment.

In this embodiment, the groove 92 is defined by an upper rim or wall 93 angled in an anterior direction, an inward-facing lateral wall 94, and a lower rim or wall 91 angled in a posterior direction. The upper rim 93 may be angled at 30 degrees, for example, anteriorly from the plane of the groove 92, and the lower rim 91 may be angled at 30 degrees, for example, posteriorly from the plane of the groove 92.

The lateral wall 94 may have a height (anterior-posterior dimension) that matches the thickness of the tabs 95 and 96. The lateral wall 94 may have a linear geometry that matches the outer-most wall of the tabs 95 and 96. The lateral wall 94 may intersect the upper and lower rims 93 and 91 to form inside corners. Compared to a curved intersection, the inside corners may provide better anterior-posterior stability of the tabs 95 and 96 inside the groove 92, and thereby provide better anterior-posterior stability of the lens 65 relative to the base 55B.

The opening of the groove 92 may have a dimension defined by the distance between the upper rim 93 and the lower rim 91 along the inside diameter of the rims 91 and 93. The opening dimension of the groove 92 may be substantially greater than the thickness of the tabs 95 and 96 to allow for easy insertion of the lens 65 into the base 55B. In one example, the opening dimension of the groove 92 is 1.5 times greater than the thickness of the tabs 95 and 96. In another example, the opening dimension of the groove 92 is 2.0 times greater than the thickness of the tabs 95 and 96. The large opening of the groove 92 allows for faster and easier insertion of the lens 65 into the base 55B.

Commercially available IOLs typically have an equatorial diameter (excluding haptics) of about 6 mm, an anterior-posterior thickness of about 0.2 mm at 6 mm diameter and 0.7 mm at the center, providing an overall volume of about 12 mm$^3$. Lens 65 is similarly dimensioned, but the base 55B adds substantially more volume. The base 55B may have an equatorial diameter (excluding haptics 54) of about 8.5 mm, an anterior-posterior thickness of about 1 mm at 8.5 mm diameter, 2.5 mm at 6 mm diameter, providing an overall volume of about 67 mm$^3$ when the lens 65 is disposed in the base 55B. Thus, the size of the combined base 55B and lens 65 is volumetrically much larger than conventional IOLs available on the market. This relatively larger volume is intended to fill the capsular bag more like a natural lens, thus increasing the stability of the base 55B and reducing post-operative migration due to the bag collapsing around the base 55B. By way of comparison, a typical natural lens has an equatorial diameter of about 10.4 mm, an anterior-posterior dimension of about 4.0 mm for a corresponding volume of about 180 mm$^3$. Due to anatomic variability, a natural lens may have a volume ranging from 130 mm$^3$ to 250 mm$^3$. Thus, the base 55B plus the lens 65 consumes about 50% to 25% of the volume of the bag after the natural lens has been extricated, whereas a conventional IOL consumes about 10% to 5% of the volume of the bag.

Figure 7A:
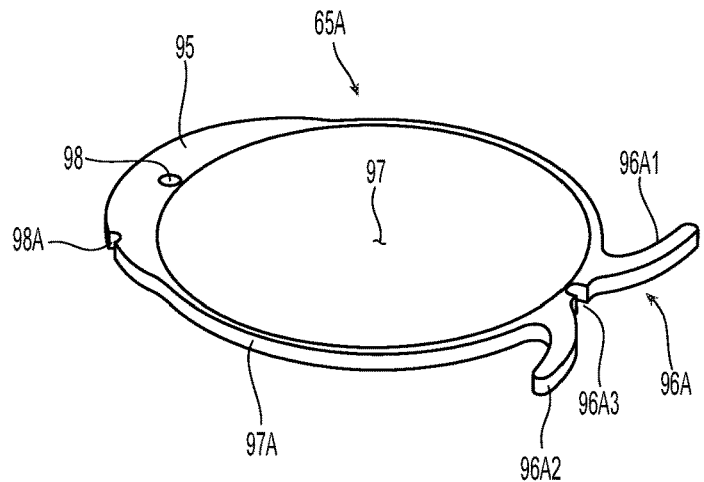
FIGS. 7A-7C are perspective and top views of an alternative lens portion of a modular IOL according to the present disclosure.
Figure 7B:
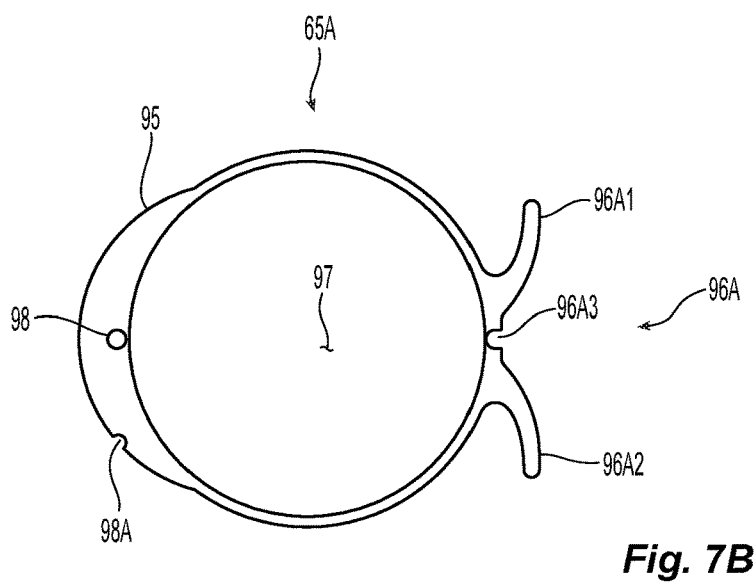

FIGS. 7A-7B illustrate an alternative lens 65A for use with the modular IOL 90. FIG. 7A is a perspective view of the alternative lens 65A, and FIG. 7B is a top (anterior) view of the lens 65A. Alternative lens 65A is similar in design and function as lens 65, except for a notch 98A provided in the fixed tab 95 and an alternative actuatable tab 96A. All similar aspects of the prior embodiment are incorporated by reference into the description of this embodiment.

Specifically, alternative lens 65A includes an optic portion 97 and one or more fixed tabs 95 and one or more actuatable tabs 96A. Optionally, fixed tab 95 may be replaced with an actuatable tab (e.g., like tab 96A). Fixed tab 95 may include a thru hole 98 so that a probe or similar device may be used to engage the hole 98 and manipulate the tab 95. Fixed tab 95 may also include a notch 98A positioned counter-clockwise of the hole 98 (or otherwise on the counter-clockwise side of the tab 95) to provide an indication that the anterior side of the lens 65A is right side up when implanted. In other words, when the lens 65A is placed in the base 55, if the notch 98A is positioned counter-clockwise of the hole 98, then the anterior side of the lens 65A is correctly positioned facing anteriorly. If the notch 98A is positioned clockwise of the hole 98, then the anterior side of the lens 65A is incorrectly positioned facing posteriorly. Other indicators of correct anterior-posterior placement of the lens 65A may be employed by providing two markers about the periphery of the lens 65A and designating their correct relative position (clockwise or counter-clockwise).

Actuatable tab 96A may be actuated between a compressed position for delivery into the hole 57 of the base 55, and an uncompressed extended position (shown) for deployment into the groove 92 of the base 55, thus forming an interlocking connection between the base 55 and the lens 65A. Actuatable tab 96A includes two members 96A1 and 96A2, each with one end connected to the peripheral rim 97A around optic 97, and the other end free, thus forming two cantilever springs. Compared to actuatable tab 96 (illustrated in FIGS. 2D-2F) which is attached at two ends to the periphery of the optic 97 and is joined in the middle like a single leaf spring, actuatable tab 96A includes two members 96A1 and 96A2 with each end attached to the peripheral rim 97A around the optic 97 and the other end free like two cantilever springs. A notch 96A3 may be formed in the peripheral rim 97A between the two members 96A1 and 96A2 to add hinge-like flexibility to the two members 96A1 and 96A2 where they attach to the peripheral rim 97A. Notch 96A3 also provides access for a probe or similar device manipulate the tab 96A into the groove 92 in the base 55.

As shown in FIGS. 7A and 7B, the two cantilever members 96A1 and 96A2 of actuatable tab 96A are attached at one end to the peripheral rim 97A around the optic 97 and extend radially outward and away from each other in an arc shape. In this configuration, and as compared to actuatable tab 96 shown in FIGS. 2D-2F, the cantilever members 96A1 and 96A2 engage the lateral wall 94 defining the groove 92 in the base 55 at two spaced-apart portions. Together with fixed tab 95, which contacts a portion of the lateral wall 94 diametrically opposite, the lens 65A is connected to the base 55 at three spaced apart locations, thus providing additional relative planar stability.

Figure 7C:
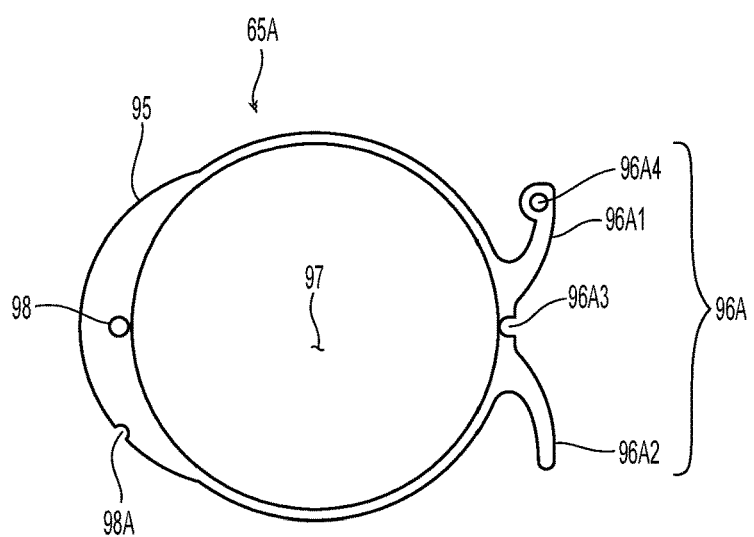

Optionally, one or both of the two cantilever members 96A1 and 96A2 may include a hole 96A4 as shown in FIG. 7C. Hole 96A4 may be sized and configured to receive an intraocular tool such as a Sinskey hook, which may be used to rotate the lens 65A when disposed in the base 55. This allows for easy rotational adjustment of the lens 65A relative to the base 55, which may be useful in making adjustments in toric applications. Such a feature may be incorporated into any of the fixed or actuatable tabs described herein.

Figure 8A:
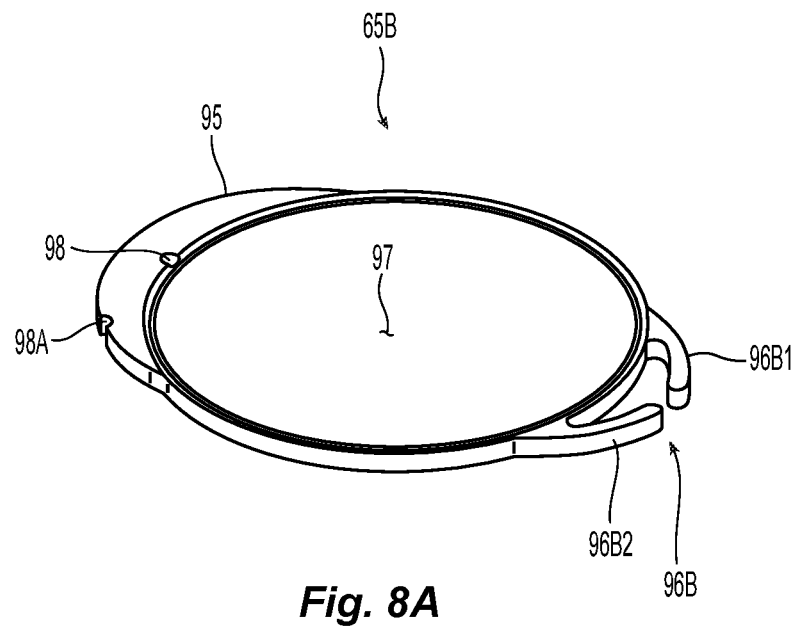
FIGS. 8A and 8B are perspective and top views of another alternative lens portion of a modular IOL according to the present disclosure.
Figure 8B:
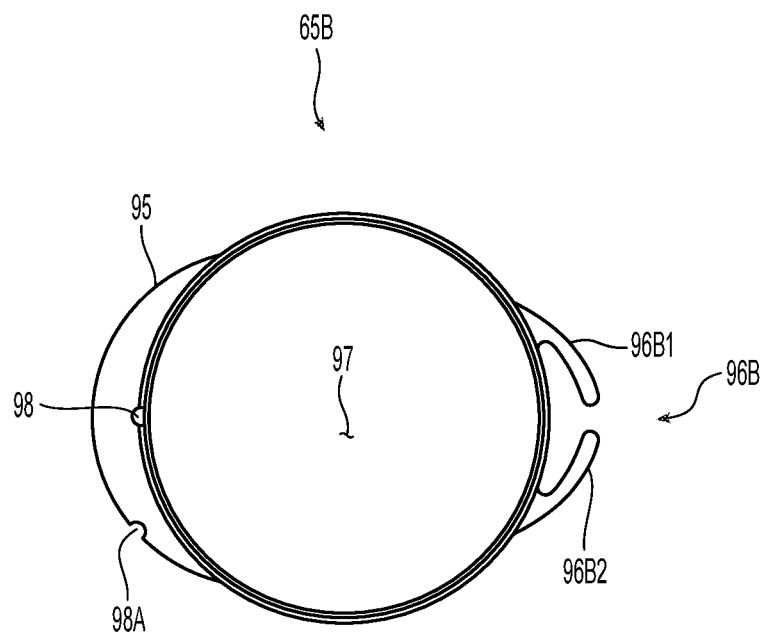

FIGS. 8A-8B illustrate yet another alternative lens 65B for use with the modular IOL 90. FIG. 8A is a perspective view of the lens 65B, and FIG. 8B is a top (anterior) view of the lens 65B. Alternative lens 65B is similar in design and function as lens 65A, except for an alternative actuatable tab 96B, which includes two cantilever members 9661 and 9662. All similar aspects of the prior embodiment are incorporated by reference into the description of this embodiment. In this embodiment, the two cantilever members 96B1 and 96B2 of actuatable tab 96B are attached at one end to the peripheral rim 97A around the optic 97 and extend radially outward and toward each other (rather than away from each other) in an arc shape. This configuration is similar to the actuatable tab 96 shown in FIGS. 2D-2F except that the members 96B1 and 96B2 are disconnected, thus forming a pair of cantilever springs rather than a leaf spring.

Optionally, drugs may be incorporated into or carried by the base 55. Using the base 55 as a carrier for drugs, as opposed to the lens 65, has a number of advantages. For example, it avoids any interference the drug or drugs may have with the optical performance of the lens 65. Also, because the base 55 doesn't require tumbling as part of the manufacturing process like the lens 65 does, drugs carried by the base 55 aren't exposed to potential damage. Drugs may be incorporated into the base 55 by connecting one or more separate drug carriers to the base 55, having the material of the base 55 act as a carrier for the drug (e.g., like a sponge), incorporating one or more drug-eluting materials into the base 55, or incorporating one or more refillable reservoirs into the base 55 that carry the drug. One or multiple portions of the base 55 may carry the drug or drugs, and these portions may be separate from each other, to avoid interaction between different drugs, for example. The portion or portions of the base 55 carrying the drug may be selectively activated by light or thermal energy (e.g., laser, UV light, etc.) to release the stored drug or drugs all at once or in a series of releases over time.

Examples of clinical indications for such drugs include wet or dry macular degeneration, open or close angle glaucoma, uveitis, posterior capsular opacification, post-op management after cataract surgery, etc. Examples of drugs that may be used for wet macular degeneration include aflibercept, bevacizumab, pegaptanib, ranibizumab, steroids, and aptamers. Examples of drugs that may be used for dry macular degeneration include complement factors, anti-oxidants and anti-inflammatory agents. Examples of drugs that may be used for open angle glaucoma include brimonidine, latanoprost, timolol, pilocarpine, brinzolamide and other drugs in the general categories of beta blockers, alpha agonists, ROCK Inhibitors, adenosine receptor agonists, carbonic anhydrase inhibitors, adrenergic and cholinergic receptor activating agents, and prostaglandin analogues. Examples of drugs that may be used for uveitis include methotrexate, antibodies, dexamethasone, triamcinolone, and other steroid agents. Examples of drugs that may be used for posterior capsular opacification include anti-proliferative, anti-mitotic, anti-inflammatory, and other medications that would inhibit the spread of lens epithelial cells. Examples of drugs that may be used for post-op management after cataract surgery include antibiotics such as fluoroquinolones, non-steroidal agents such as ketorolacs, and steroids such as prednisolones. Other medications that may be used to treat various ocular diseases and conditions include: anti-fibrotic agents, antiinflammatory agents, immunosuppressant agents, anti-neoplastic agents, migration inhibitors, anti-proliferative agents, rapamycin, triamcinolone acetonide, everolimus, tacrolimus, paclitaxel, actinomycin, azathioprine, dexamethasone, cyclosporine, bevacizumab, anti-VEGF agents, anti-IL-1 agents, canakinumab, anti-IL-2 agents, viral vectors, beta blockers, alpha agonists, muscarinic agents, steroids, antibiotics, non-steroidal antiinflammatory agents, prostaglandin analogues, ROCK inhibitors, nitric oxide, endothelin, matrixmetalloproteinase inhibitors, CNPA, corticosteroids, and antibody-based immunosuppresants. These drugs may be used individually or in combination, depending on the patient's particular clinical indication.

Also, the portion or portions of the base 55 carrying the drug or drugs may face a particular direction or directions while other directions are masked or blocked to increase the concentration of the drug on a specific portion of the lens capsule. For example, posterior ocular structures may be the focus of drug delivery (e.g., to mitigate macular degeneration), and/or anterior ocular structures may be the focus of drug delivery (e.g., to deliver glaucoma drugs adjacent the angle, to deliver drugs for uveitis or post-op management after cataract surgery).

Figure 9:
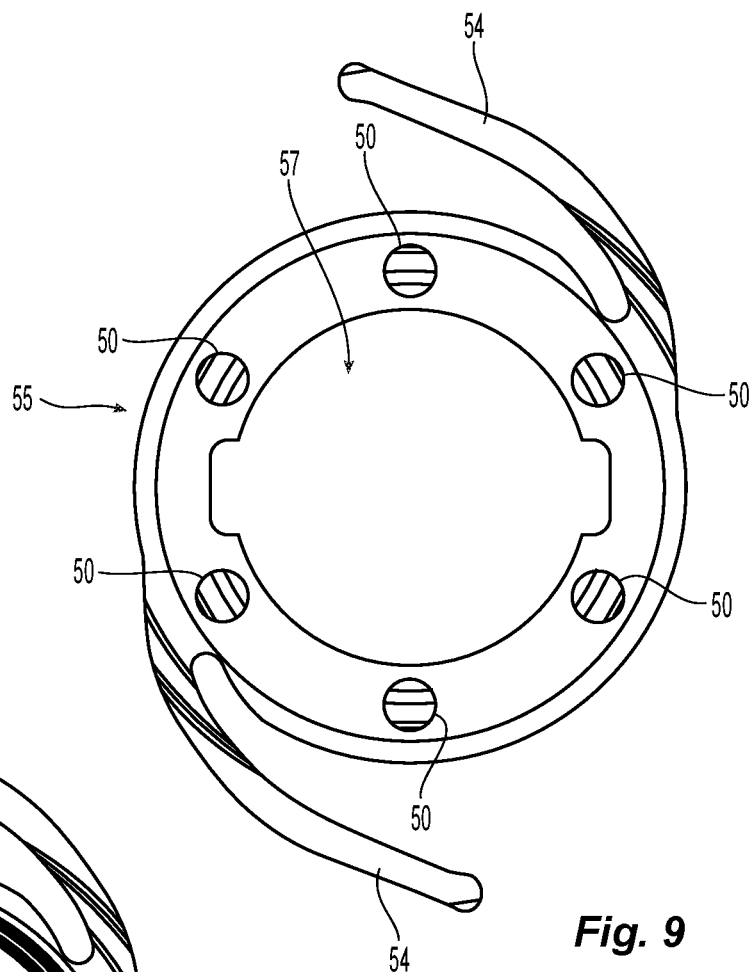
FIG. 9 is a schematic top view of an alternative lens portion of a modular IOL incorporating drug delivery capabilities according to the present disclosure.

By way of example, FIG. 9 shows a top (anterior) view of the base 55, which incorporates one or more drug carriers 50. As shown, the drug carriers 50 are spaced around the circumference of the anterior side of the body of the base 55. The drug carriers 50 may comprise a refillable reservoir (e.g., silicone vessel), an eluting porous material (e.g., biocompatible sponge), a biodegradable or bioerodable material (e.g., PLGA), etc. The reservoir may also be targeted to expose drugs to the aqueous environment through laser, UV light, RF signal, magnetic manipulation or other methods for remotely removing a barrier to diffusion. The carriers 50 may be placed on the surface of the base 55, or embedded, for example. To focus the delivery of drugs to a particular area of the eye, the carriers 50 may be exposed on one side (e.g., the anterior side as shown) while the material of the base 55 covers the other sides.

Similarly, one or more microelectronic sensors may be incorporated into or carried by the base 55. Using the base 55 as a carrier for sensors, as opposed to the lens 65, has a number of advantages. For example, it avoids any interference the sensors may have with the optical performance of the lens 65. Also, because the base 55 doesn't require tumbling as part of the manufacturing process like the lens 65 does, sensors carried by the base 55 aren't exposed to potential damage.

Figure 10:
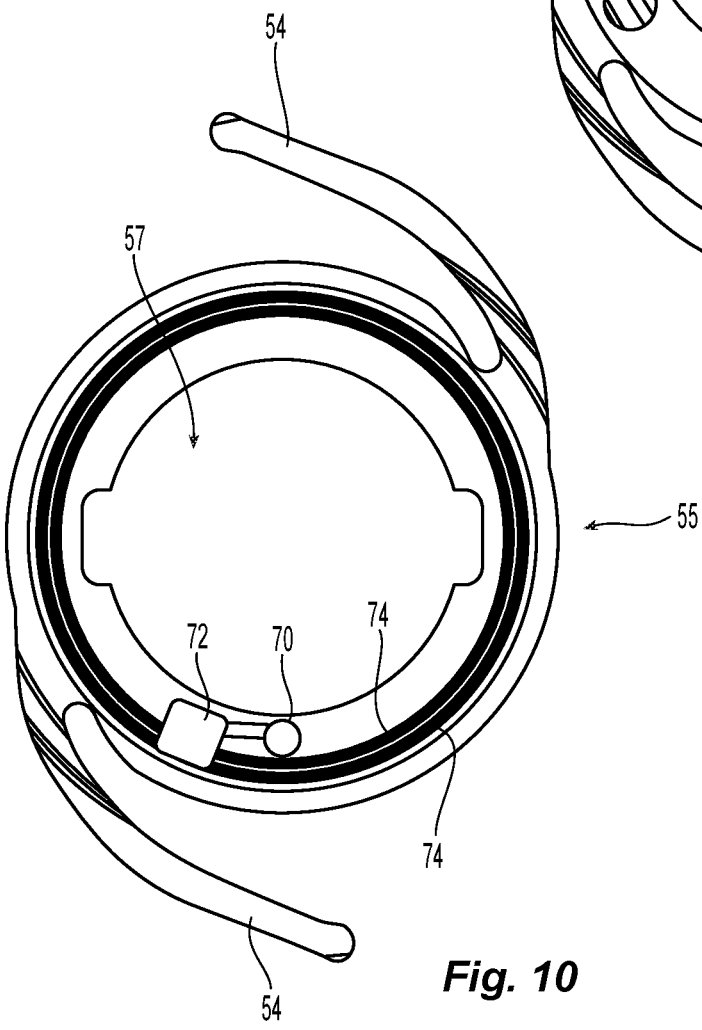
FIG. 10 is a schematic top view of an alternative lens portion of a modular IOL incorporating sensor capabilities according to the present disclosure.

As shown in FIG. 10 which is a top (anterior) view of a base 55, a sensor 70 may be attached or embedded in the base 55 in a manner similar to drug carrier 50 described with reference to FIG. 9. The sensor 70 may be connected to an integrated control circuit 72, which is connected to an antenna 74. The control circuit 72 may include a transmitter or transceiver circuit to wirelessly transmit sensor data to an external device via antenna 74. The control circuit 72 may include a power circuit that receives electrical power via an inductive link to an external power source. Examples of suitable sensors that may be incorporated into or carried by the base 55 include biological sensors such as a glucose sensor, an electrolyte sensor, a protein sensor, a temperature sensor, a conductivity sensor, an electric field sensor, a pressure sensor (e.g., for measuring intra-ocular pressure), a pulse oximeter sensor, or a photo sensor to support artificial vision. Examples of microelectronic sensors for use with contact lenses are described in U.S. Patent Application Publications 2014/0085599, 2014/0084489, 2014/0085602, and 2014/0087452, 2014/0085600, 2014/0088381, 2014/0192311, 2014/0194710, 2014/0194713, 2014/0194773, 2014/0098226 and 20140081178, and PCT Publication WO/2014/204575 which are incorporated herein by reference. Such microelectronic sensors for use with contact lenses may be hermetically sealed in the base 55 for implant applications in the eye. The sensor 70 may include a permeable cover for direct biological interface applications (glucose sensor, electrolyte sensor, protein sensor, etc.).

Alternatively, the sensor 70 may include an impermeable cover for indirect biological interface applications (pressure sensor, temperature sensor, conductivity sensor, electric field sensor, etc.).

The foregoing discussion of the disclosure has been presented for purposes of illustration and description. The foregoing is not intended to limit the disclosure to the form or forms disclosed herein. Although the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

We claim:

1. A device configured for insertion into an eye, the device comprising:
    an anterior section surrounding an anterior opening, wherein a portion of the anterior section is angled such that the anterior section extends farther toward an anterior direction as the anterior section extends towards the anterior opening;
    a posterior section surrounding a posterior opening, wherein a portion of the posterior section is angled such that the posterior section extends farther toward a posterior direction as the posterior section extends towards the posterior opening;
    an in-ward facing lateral wall extending between the anterior and the posterior sections;
    a passage extending through the device from the anterior opening to the posterior opening; and
    a recess surrounding the passage, wherein the recess is bordered by a posterior surface of the anterior section, the in-ward facing lateral wall, and an anterior surface of the posterior section,
    wherein the recess comprises a first angle formed by the in-ward facing lateral wall and the posterior surface of the anterior section and a second angle formed by the in-ward facing lateral wall and the anterior surface of the posterior section and the recess is configured to surround a portion of a lens configured to be received in the recess.

2. The device of claim 1, wherein an axial thickness measured between an anterior surface of the anterior section and a posterior surface of the posterior section is at least approximately 1 mm.

3. The device of claim 2, wherein the axial thickness is between approximately 1 mm and 2.5 mm.

4. The device of claim 1, wherein the anterior section is angled in the anterior direction at approximately 30 degrees relative to an equatorial plane of the device.

5. The device of claim 1, wherein the posterior section is angled in the posterior direction at approximately 30 degrees relative to an equatorial plane of the device.

6. A device configured for insertion into an eye, the device comprising:
    an annular base, comprising:
        a central longitudinal axis,
        an equatorial plane extending perpendicular to the central longitudinal axis,
        an anterior section surrounding an anterior opening, wherein the anterior section has an anterior surface and a posterior surface, and wherein the anterior and the posterior surfaces extend transverse to the equatorial plane,
        a posterior section surrounding a posterior opening,
        an in-ward facing lateral wall extending between the anterior and the posterior sections,
        a passage extending through the base from the anterior opening to the posterior opening, and
        a recess surrounding the passage, wherein the recess is bordered by the posterior surface of the anterior section, the in-ward facing lateral wall, and an anterior section of the posterior section,
    wherein the recess comprises a first angle formed by the in-ward facing lateral wall and the posterior surface of the anterior section and a second angle formed by the in-ward facing lateral wall and the anterior surface of the posterior section and the recess is configured to surround a portion of a lens configured to be received in the recess.

7. The device of claim 6, wherein the first angle is an obtuse angle.

8. The device of claim 6, wherein the anterior section includes a radially inner surface extending from the anterior surface to the posterior surface of the anterior section.

9. The device of claim 6, wherein an axial thickness of the annular base is at least approximately 1 mm.

10. The device of claim 6, wherein an axial thickness of the annular base is between approximately 1 mm and 2.5 mm, and wherein a diameter of the annular base is approximately 8.5 mm.

11. The device of claim 6, wherein a ratio of an axial thickness of the annular base to a diameter of the annular base is between approximately 0.12 and 0.29.

12. A device configured for insertion into an eye, the device comprising:
    an annular base, comprising:
        an anterior section surrounding an anterior opening, wherein the anterior section has a posterior surface,
        a posterior section surrounding a posterior opening,
        an in-ward facing lateral wall extending between the anterior and the posterior sections,
        a passage extending through the base from the anterior opening to the posterior opening, and
        a recess surrounding the passage, wherein the recess is defined by the posterior surface of the anterior section, the in-ward facing lateral wall, and an anterior section of the posterior section,
    wherein the recess comprises a first angle formed by the in-ward facing lateral wall and the posterior surface of the anterior section and a second angle formed by the in-ward facing lateral and the anterior surface of the posterior section, wherein the first angle is an obtuse angle and further wherein the recess is configured to surround a portion of a lens configured to be received in the recess.

13. The device of claim 12, wherein the anterior opening is wider than the posterior opening.

14. The device of claim 12, wherein a ratio of an axial thickness of the annular base to a diameter of the annular base is between approximately 0.12 and 0.29.

15. The device of claim 1, further comprising a pair of haptics.

16. The device of claim 6, wherein the annular base further comprises a pair of haptics.

17. The device of claim 1, wherein the lens include at least one tab.

18. The device of claim 17, wherein the wall has a linear geometry that matches an outer-most wall of the at least one tab.

* * * * *